US008357781B2

(12) United States Patent
Johnson-Wood et al.

(10) Patent No.: US 8,357,781 B2
(45) Date of Patent: Jan. 22, 2013

(54) NEUROACTIVE FRAGMENTS OF APP

(75) Inventors: Kelly Johnson-Wood, Scotts Valley, CA (US); Peter Seubert, San Francisco, CA (US); Thierry Bussiere, Cambridge, MA (US)

(73) Assignee: Janssen Alzheimer Immunotherapy, Little Island, County Cork (IE)

( * ) Notice: Subject to any disclaimer, the term of this patent is extended or adjusted under 35 U.S.C. 154(b) by 0 days.

(21) Appl. No.: 11/809,552

(22) Filed: Jun. 1, 2007

(65) Prior Publication Data

US 2008/0044406 A1 Feb. 21, 2008

Related U.S. Application Data

(60) Provisional application No. 60/810,245, filed on Jun. 1, 2006.

(51) Int. Cl.
*C07K 16/00* (2006.01)
*C12P 21/08* (2006.01)

(52) U.S. Cl. ............. 530/388.15; 530/387.1; 530/387.3; 530/387.9

(58) Field of Classification Search ........................ None
See application file for complete search history.

(56) References Cited

U.S. PATENT DOCUMENTS

| | | | | |
|---|---|---|---|---|
| 5,196,510 A * | 3/1993 | Rodwell et al. | ................ | 530/324 |
| 5,472,693 A * | 12/1995 | Gourlie et al. | ............. | 424/133.1 |
| 5,530,101 A * | 6/1996 | Queen et al. | ............... | 530/387.3 |
| 5,624,659 A * | 4/1997 | Bigner et al. | ................ | 424/1.49 |
| 5,665,595 A * | 9/1997 | Petell et al. | .................... | 435/332 |
| 6,018,024 A | 1/2000 | Seubert et al. | | |
| 6,717,031 B2 | 4/2004 | Games et al. | | |
| 6,750,324 B1 | 6/2004 | Schenk et al. | | |
| 2003/0165496 A1* | 9/2003 | Basi et al. | .................. | 424/141.1 |

FOREIGN PATENT DOCUMENTS

WO   WO 2008/042024 A2   4/2008

OTHER PUBLICATIONS

Arai 1990 (Proc Natl Acad Sci USA 87:2249-2253).*
Yokoyama 1999 (Current Protocols in Cell Biology 16.1.1-16.1.17).*
Arbel 2005 (Proc Natl Acad Sci USA 102:7718-7723).*
Alzforum APP mutations table, updated Apr. 2, 2010.*
Alzheimer Disease & Frontotemporal Dementia Database, Mutations in APP, accessed Feb. 11, 2011.*
PCT International Preliminary Report on Patentability (Chapter I) of Dec. 3, 2008 for application PCT/US2007/013128.
PCT Search Report of Sep. 13, 2008 for application PCT/US2007/013128.
PCT Written Opinion of Sep. 17, 2008 for application PCT/US2007/013128.
Games et al., "Alzheimer-type neuropathology in transgenic mice overexpressing V717F β-amyloid precursor protein," *Nature* 373:523-527 (1995).
Hardy et al., "Amyloid, the presenilins and Alzheimer's disease," *Trends Neurosci.* 20:154-159 (1997).
Kennedy et al., "Only Kunitz-Inhibitor-Containing Isoforms of Secreted Alzheimer Amyloid Precursor Protein Show Amyloid Immunoreactivity in Normal Cerebrospinal Fluid," *Neurodegeneration* 1: 59-64 (1992).
Mori et al., "Phospho-App Immunoreactivity (IR) in the Brains of 2 Models of Alzheimer's Disease (AD): Down Syndrome (DS) and App Transgenic (TG) Mice," Program No. 427.16, *2001 Neuroscience Meeting Planner. San Diego, CA: Society for Neuroscience*, (2001). Online. Abstract Only.
Oltersdorf et al., "The Alzheimer Amyloid Precursor Protein, Identification of a Stable Intermediate in the Biosynthetic/Degradative Pathway," *J. Biol. Chem.* 265(8):4492-4497 (1990).
Supplementary European Search Report and European Search Opinion for application EP2035448 mailed Oct. 1, 2010.
Wirths et al., "Intraneuronal Aβ accumulation precedes plaque formation in β-amyloid precursor protein and presenilin-1 double-transgenic mice," *Neuroscience Letters* 306:116-120 (2001).
Xia et al., "Interaction between amyloid precursor protein and presenilins in mammalian cells: Implications for the pathogenesis of Alzheimer disease," *Proc. Nat'l Acad. Sci. USA* 94(15):8208-8213 (1997).

* cited by examiner

*Primary Examiner* — Olga N Chernyshev
(74) *Attorney, Agent, or Firm* — Alston & Bird LLP

(57) ABSTRACT

The application provides novel neuroactive fragments of human amyloid precursor protein (APP). The fragments include sequence from the Aβ region of APP but also extend upstream. The fragments are soluble in aqueous solution most bands are about 10 kDa and above and do not correspond with the expected molecular weight of a dimer or trimer. The fragments and subfragments thereof can be used as immunogens in methods of immunotherapy to treat Alzheimer's and other amyloidogenic diseases characterized by deposits of Aβ in the brain. Antibodies to the part of the fragment upstream from APP or the interface between Aβ and the upstream sequence can also be used in such therapeutic method. The fragments are also useful as markers, which can be detected for diagnosis or prognosis of disease or for screening agents.

2 Claims, 12 Drawing Sheets

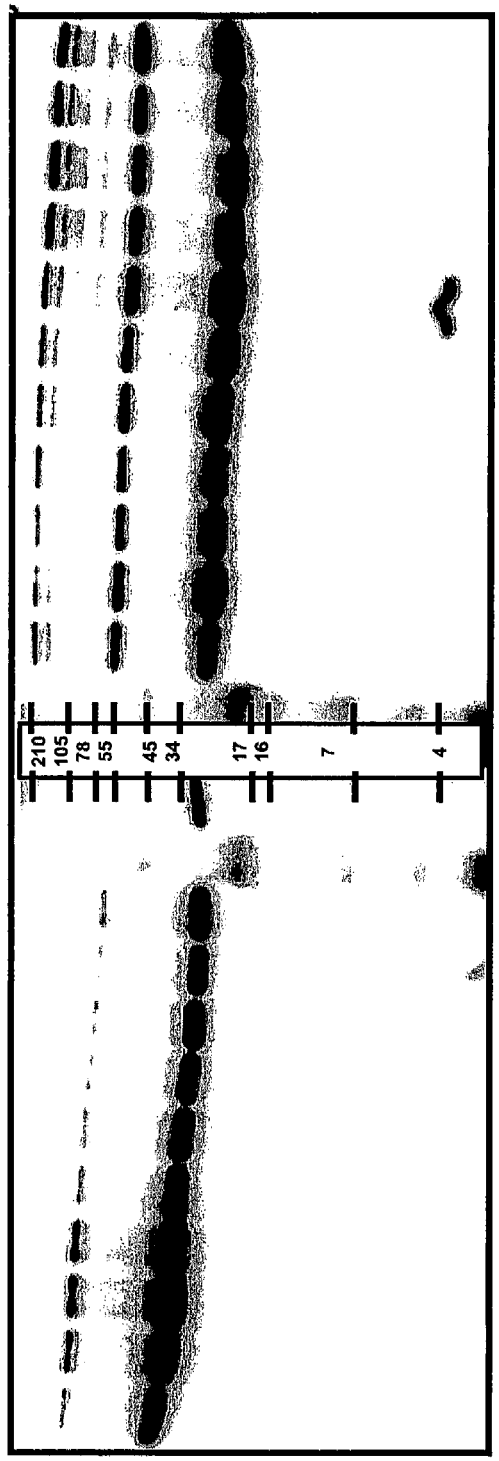
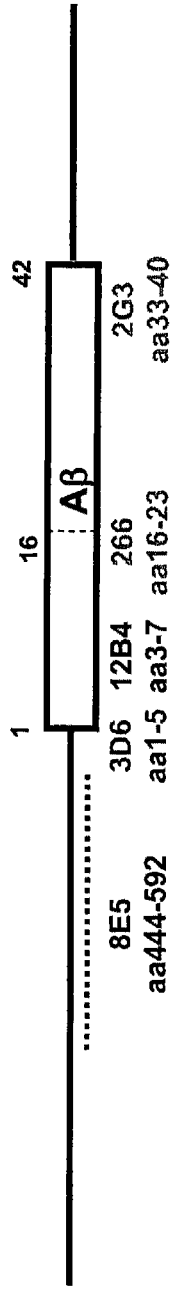
Fig. 5A

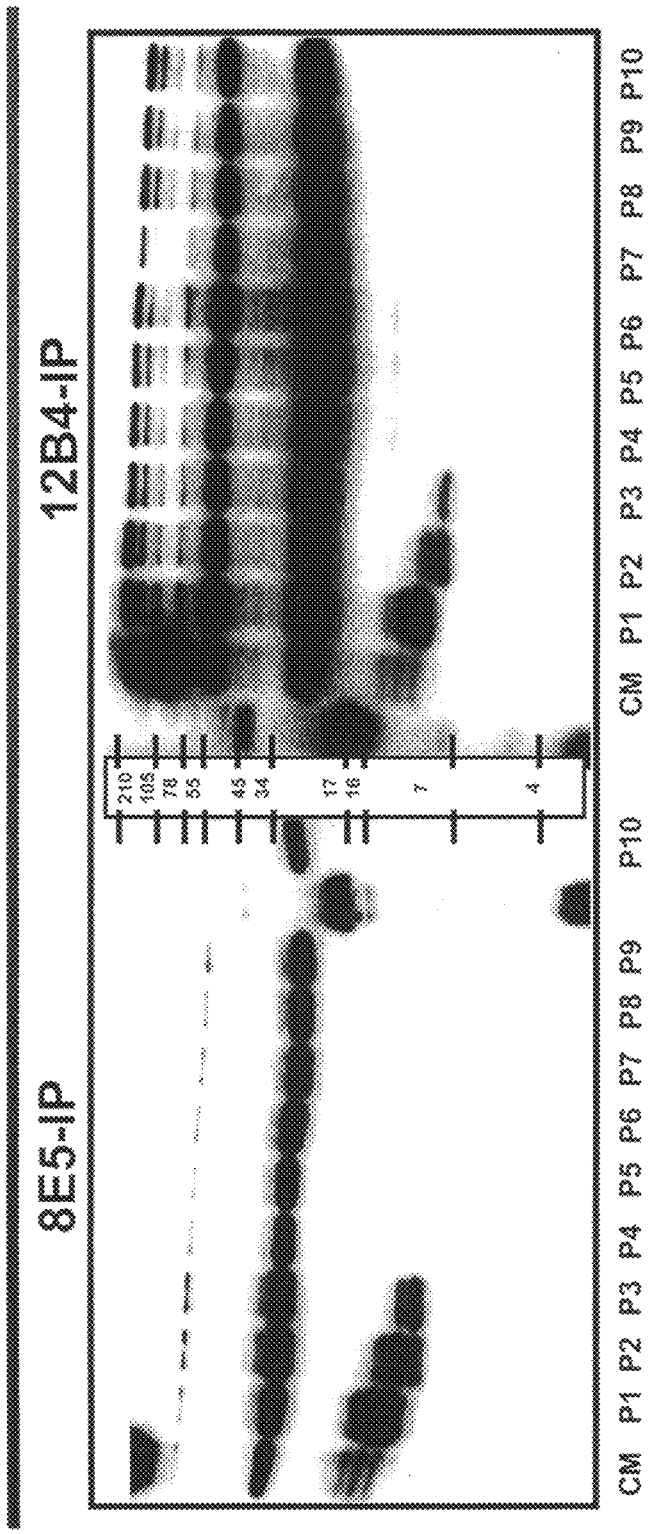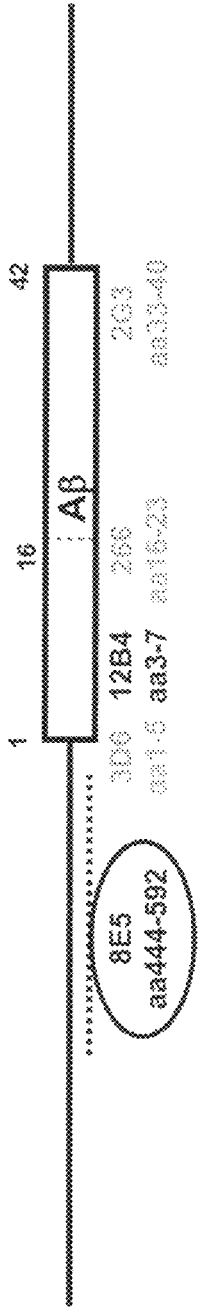

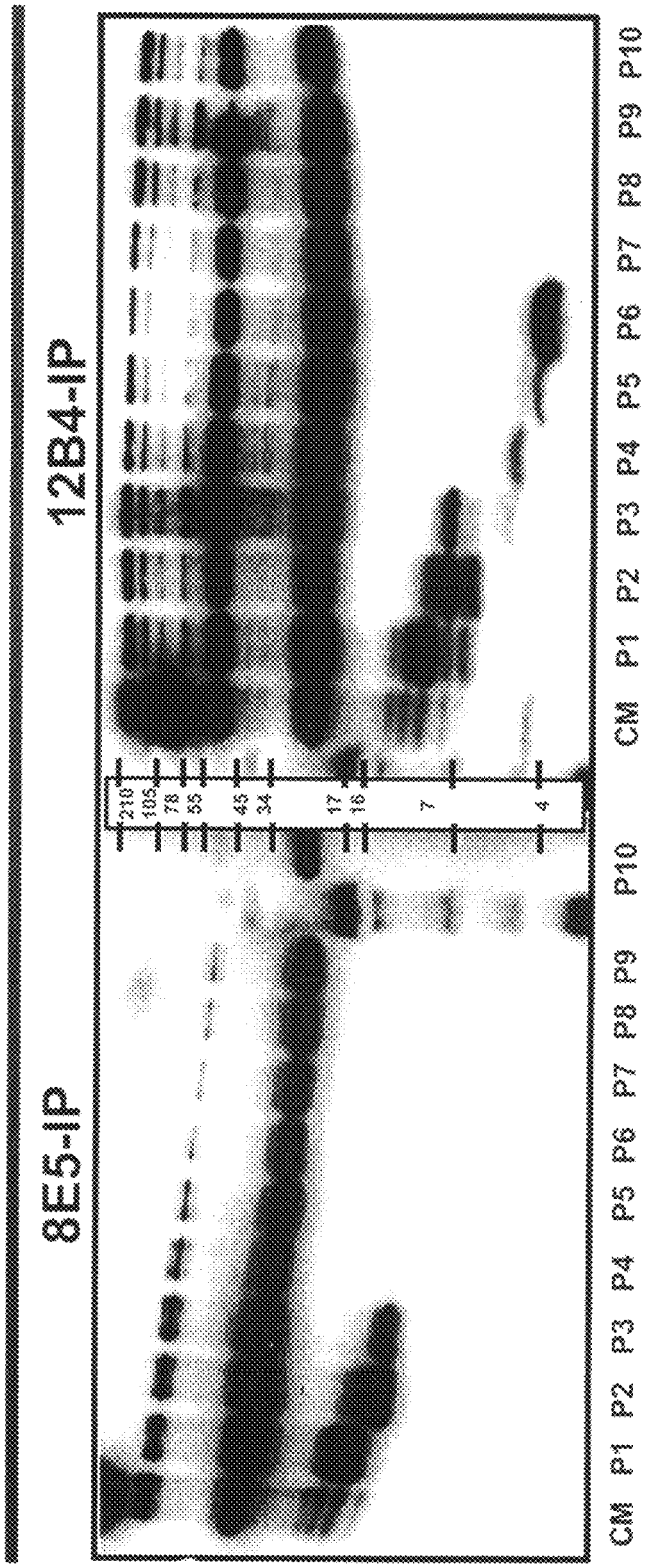
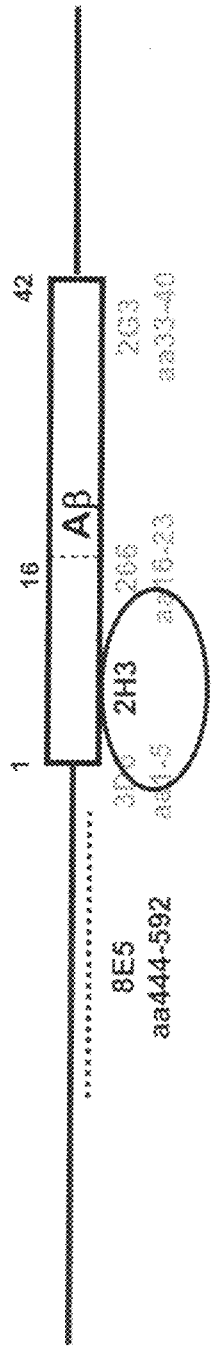
Fig. 5C

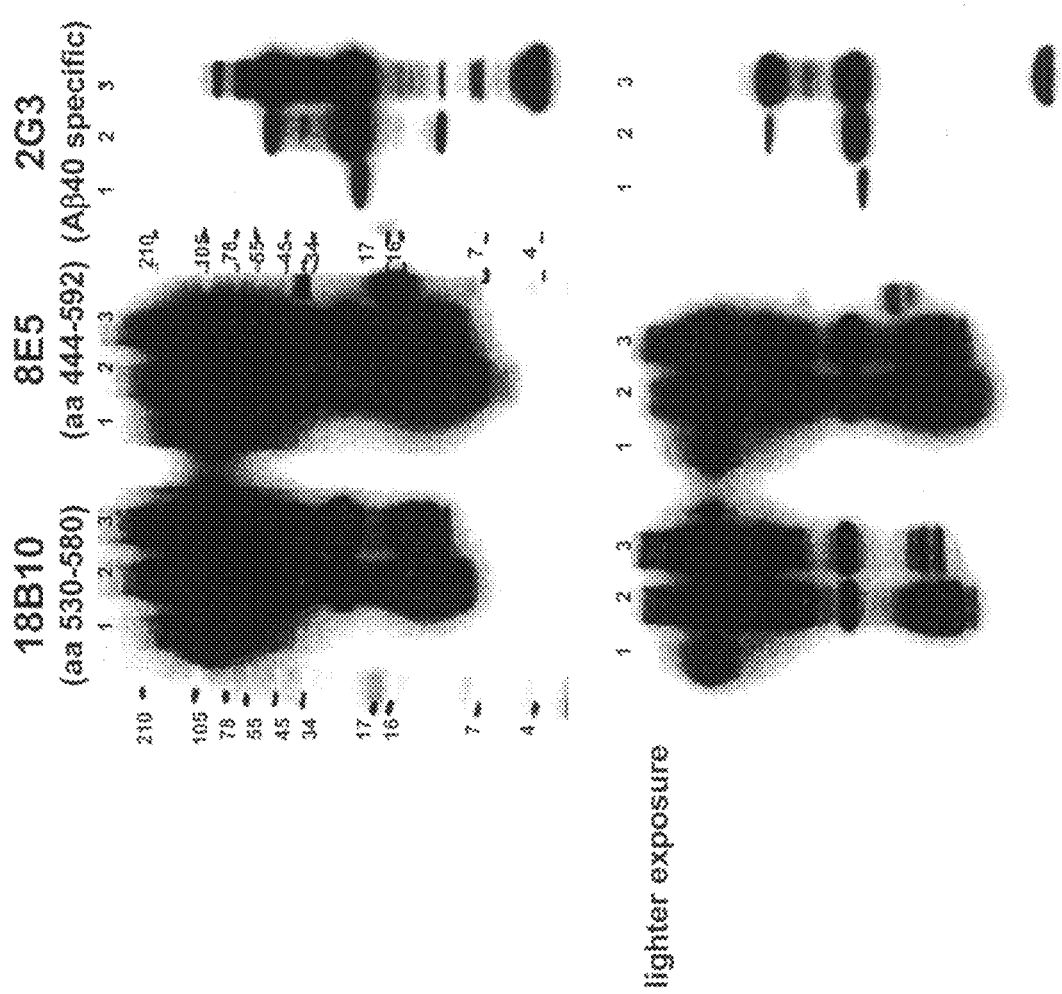

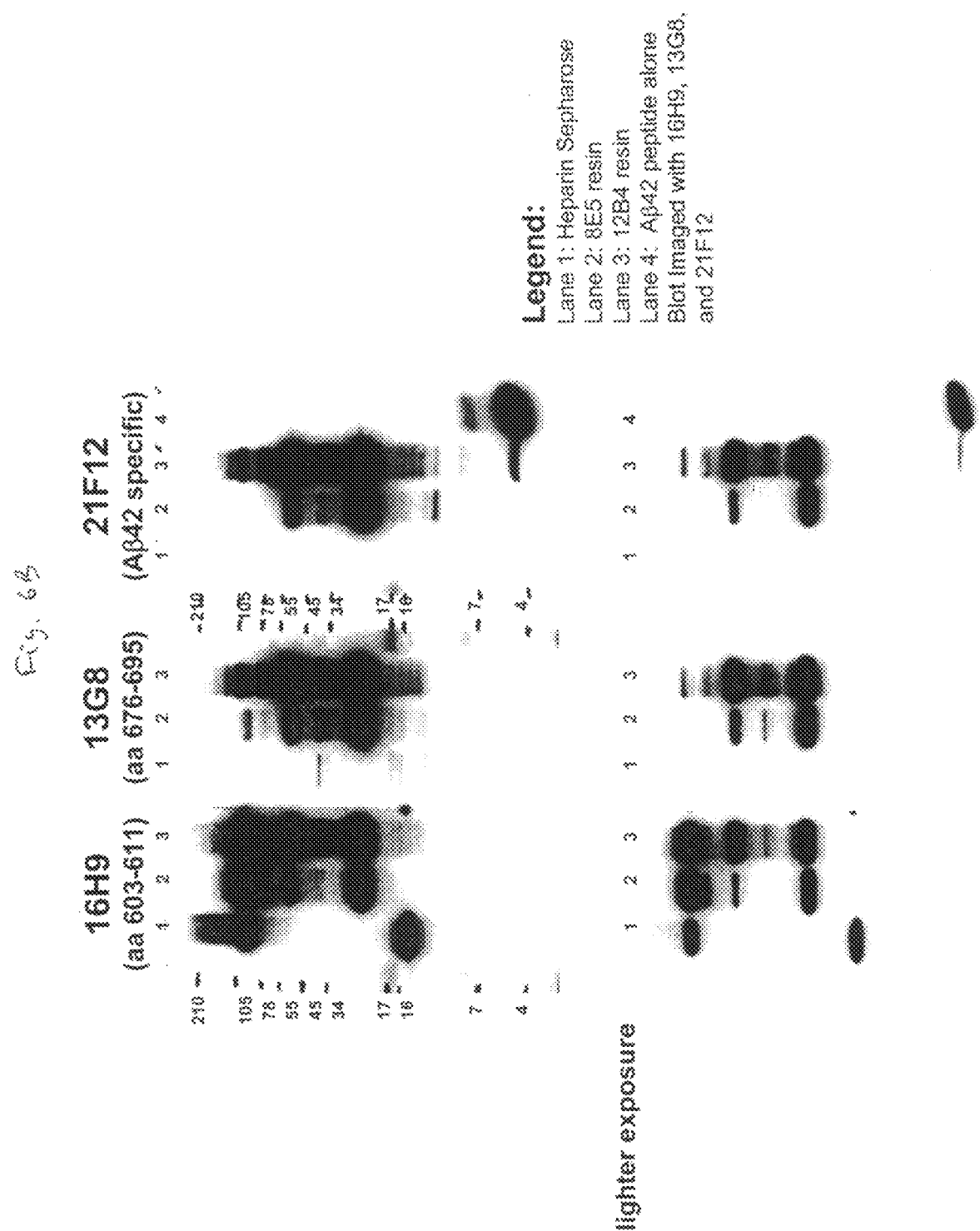

Fig. 7

7PA2 CM / 8E5 – N-Terminal Sequencing Results

8E5 – APP$_{444-592}$

$^{444}$ $^{475}$
{DPKKAAQIRSQVMTHLRVIYERMNQSLLYN $^{476}$ $^{505}$
VPAVAEEIQDEVDELLQKEQNYSDDVLANM $^{506}$ $^{535}$
ISEPRISYGN $^{516}$DALMPSLTET$^{525}$ KTTVELLPVN $^{536}$ $^{565}$
GEFSLDDLQP$^{545}$ WHSFGADSVPANTENEVEPV
 $^{548}$ $^{551}$
 P V $^{566}$ $^{595}$
DARPAADRGLTTRPGSGLTNIKTEEIS}EVK
 $^{592}$ $^{596}$
M

Aβ$_{1-42}$

DAEFRHDSGYEVHHQKLVFFAEDVGSNKGAIIGLMVGGVVIA
$^{1}$ $^{4}$ $^{19}$ $^{20}$

F = phenylalanine

NEUROACTIVE FRAGMENTS OF APP

CROSS-REFERENCE TO RELATED APPLICATION

The present application is a nonprovisional and claims the benefit of 60/810,245 filed Jun. 1, 2006, incorporated by reference in its entirety for all purposes.

BACKGROUND OF THE INVENTION

Alzheimer's disease (AD) is a progressive disease resulting in senile dementia. See generally Selkoe, TINS 16, 403-409 (1993); Hardy et al., WO 92/13069; Selkoe, J. Neuropathol. Exp. Neurol. 53, 438-447 (1994); Duff et al., Nature 373, 476-477 (1995); Games et al., Nature 373, 523 (1995). Broadly speaking, the disease falls into two categories: late onset, which occurs in old age (65+ years) and early onset, which develops well before the senile period, i.e., between 35 and 60 years. In both types of disease, the pathology is the same but the abnormalities tend to be more severe and widespread in cases beginning at an earlier age. The disease is characterized by at least two types of lesions in the brain, senile plaques and neurofibrillary tangles. Senile plaques are areas of disorganized neuropil up to 150 µm across with extracellular amyloid deposits at the center visible by microscopic analysis of sections of brain tissue. Neurofibrillary tangles are intracellular deposits of microtubule associated tau protein consisting of two filaments twisted about each other in pairs.

The principal constituent of the plaques is a peptide termed Aβ or β-amyloid peptide. Aβ peptide is an internal fragment of 39-43 amino acids of a precursor protein termed amyloid precursor protein (APP). Several mutations within the APP protein have been correlated with the presence of Alzheimer's disease. See, e.g., Goate et al., Nature 349, 704) (1991) (valine$^{717}$ to isoleucine); Chartier Harlin et al. Nature 353, 844 (1991)) (valine$^{717}$ to glycine); Murrell et al., Science 254, 97 (1991) (valine$^{717}$ to phenylalanine); Mullan et al., Nature Genet. 1, 345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ (see Hardy, TINS 20, 154 (1997)).

The pathogenic role of the amyloid peptide aggregated into plaques has been known for many years. However, severity of dementia is weakly correlated with the density of plaques, whereas a significant correlation exists with the levels of soluble Aβ (McLean et al., Ann. Neurol. 1999, 46:860-866). Recent studies have suggested that Aβ oligomers are implicated in synaptotoxicity and memory impairment in hAPP transgenic mice (Mucke et al., J Neurosci. 20:4050-4058 (2000); Morgan et al., Nature 408:982-985 (2000), Dodart et al., Nat Neurosci, 5:452-457 (2002). Aβ oligomers, but not monomers or fibrils, also inhibit hippocampal long-term potentiation (Walsh et al., Nature 416:535-539 (2002). The primary structure of the neurotoxic species of the "Aβ oligomer" is an area of active investigation. It has been suggested that the neurotoxic species is an oligomer of the Aβ peptides that begin at position 2 of Aβ (the alanine following the asparagines) (Podlisny, M., et al. JBC (1995) 270: 9564-9570.

SUMMARY OF THE CLAIMED INVENTION

The invention provides an antibody that specifically binds to an epitope within residues 444-595 or 444-596 of human amyloid precursor protein (APP695 numbering). Optionally, the antibody lacks specific binding to guinea pig amyloid precursor protein. Optionally, the antibody specifically binds to an epitope within residues 551-570 of human amyloid precursor protein. Optionally, the antibody specifically binds to an epitope within residues 530-580 of human amyloid precursor protein. Optionally, the antibody specifically binds to an epitope within residues 676-695 of human amyloid precursor protein. Optionally, the antibody specifically binds to an epitope within residues 545 to 555 of human amyloid precursor protein. Optionally, the antibody competes with monoclonal antibody 8E5 for specific binding to human amyloid precursor protein. Optionally, the antibody competes with 18B10 for specific binding to human amyloid precursor protein. Optionally, the antibody is a humanized, or chimeric form of 8E5 or 18B10. Optionally, the antibody is a monoclonal antibody.

The invention further provides a method of prophylactically or therapeutically treating Alzheimer's disease, comprising administering to a patient suffering from or at risk of the disease a therapeutically effective regime of a fragment comprising at least four contiguous residues between amino acids 516 and 595 or 596 of APP, and thereby prophylactically or therapeutically treating the disease. Optionally, the fragment comprises at least 5 contiguous residues between amino acids 551 and 595 or 596 of APP. Optionally, the fragment comprises at least 7 contiguous residues between amino acids 544 and 596 or 597 of APP. Optionally, the fragment comprises residues 551 to 595 or 596 of APP. Optionally, the fragment comprises residues 551-638 of APP. Optionally, the administering administers a plurality of fragments each comprising at least 4 contiguous amino acids between residues 551 and 595 or 596 of APP. Optionally, the fragment comprises from 4 to 20 contiguous amino acids between residues 551 and 595 or 596 of APP. Optionally, the fragment comprises from 4-20 contiguous amino acids between residues 516 to 595 or 596 of APP. Optionally, the fragment comprises from 4 to 10 contiguous amino acids between residues 551 and 595 or 596 of APP. Optionally, the fragment comprises from 4 to 10 contiguous amino acids between residues 516 and 595 or 596 of APP. Optionally, the fragment comprises first and second segments, the first segment being a segment of Aβ and the second segment being a segment of APP upstream of Aβ. Optionally, the first and second segments are contiguous segments of human APP. Optionally, the fragment is linked to a carrier as a conjugate, wherein the carrier helps elicits an immune response comprising antibodies to the fragment. Optionally, the method further comprises administering an adjuvant to the patient, wherein the adjuvant helps elicit an immune response comprising antibodies to the fragment. Optionally, the method further comprises administering an antibody to Aβ or an immunogen that generates the antibody. Optionally, the immunogen is administered and the immunogen is a fragment of Aβ.

The invention further provides a method of prophylactically or therapeutically treating Alzheimer's disease, comprising administering to a patient suffering from or at risk of the disease a therapeutically effective regime of either (a) an antibody that specifically binds to an epitope within residues 516 and 595 of human APP or (b) an immunogen that generates such an antibody, and thereby prophylactically or therapeutically treating the disease.

Optionally, the antibody specifically binds to an epitope with residues 530 and 595 of human APP. Optionally, the antibody is any antibody defined above. Optionally, the antibody is an end-specific antibody that binds to the N-terminus of a fragment of APP, the N-terminus being an amino acid residue between residues 535 and 555. Optionally, the antibody is an end-specific antibody that binds to the N-terminus of APP516-638 or APP536-638. Optionally, the method further comprises administering an antibody to Aβ or an immunogen that generates the antibody. Optionally, the immunogen is administered and the immunogen is a fragment of Aβ.

The invention further provides a method of screening an agent for activity useful for treating Alzheimer's disease, comprising: contacting a nonhuman transgenic animal with an agent, the nonhuman transgenic animal comprising a genome comprising a segment encoding APP, wherein the segment is expressed to amyloid precursor protein, which is processed to Aβ and other fragments; extracting an aqueous soluble fragment of APP of 50-150 amino acids, comprising at least 25 amino acids between positions 551 and 595 or 596 of APP, and comparing the amount of the soluble fragment of APP with that from a control transgenic mouse not treated with the agent, wherein a reduction in the amount of the soluble fragment is an indication that the agent has activity useful for treating Alzheimer's disease. Optionally, the APP is human APP. Optionally, the fragment comprises residues 551 to 638 of human APP. Optionally, the fragment can be specifically bound by antibody 8E5 and/or 18B10. Optionally, the fragment is APP516-638, APP516-639, APP536-638 or APP536-639.

The invention further provides a method of screening an agent for activity useful for treating Alzheimer's disease, comprising: contacting an isolated cell with an agent, the cell comprising a nucleic acid encoding APP, wherein the nucleic acid is expressed to amyloid precursor protein, which is processed to Aβ and other fragments; detecting in culture medium an aqueous soluble fragment of APP of 50-150 amino acids, comprising at least 25 amino acids between positions 551 and 595 or 596 of APP; and comparing the amount of the soluble fragment of APP with that from a control cell not treated with the agent, wherein a reduction in the amount of the soluble fragment is an indication that the agent has activity useful for treating Alzheimer's disease. Optionally, the isolated cell is transfected with a construct comprising a nucleic acid encoding APP. Optionally, the aqueous soluble fragment is APP516-638, APP56-639, APP536-638 or APP536-639.

The invention further provides a method of screening an agent for activity useful in treating Alzheimer's disease, comprising contacting an aqueous soluble fragment of APP of 50-150 amino acids, comprising at least 25 amino acids between positions 551 and 595 or 596 of APP with a population of cells and an agent; and comparing the number of viable cells compared with those remaining from a control population of cells contacted with the soluble fragment without the agent, an increase of viable cells in the presence of the agent providing an indication that the agent has activity useful in treating Alzheimer's disease.

Optionally, the cells are neuronal cells. Optionally, the aqueous soluble fragment is APP516-638, APP516-639, APP536-638 or APP536-639.

The invention further provides an isolated fragment of amyloid precursor protein of 50-150 amino acids, comprising at least 25 amino acids between positions 551 and 595 or 596 of human APP. The isolated fragment optionally comprises residues 551 to 638 of human APP. The isolated fragment optionally consists of residues 551 to 638 of human APP. Optionally, the fragment is no more than 100 amino acids long. Optionally, the fragment is specifically bound by antibody 8E5 and/or 18B10. Optionally, the fragment is APP516-638, APP516-639, APP536-638 and APP536-639.

The invention further provides an antibody that specifically binds to human amyloid precursor protein at an epitope including residues 595 and 596 of human amyloid precursor protein. The invention further provides an antibody that specifically binds to human amyloid precursor protein at an epitope including residues 596 and 597 of human amyloid precursor protein.

The invention further provides an end specific antibody that specifically binds to the N-terminus of a fragment of human APP, wherein the N-terminal amino acid is located between residues 535 and 555 of human APP.

The invention further provides an end-specific antibody of claim that specifically binds to the N-terminus of APP516-638, APP516-639, APP536-638 or APP536-639.

BRIEF DESCRIPTION OF THE DRAWINGS

FIGS. 5A, B, C: SEC of 7PA2 CM. Fractions Immunoprecipitated with 8E5-Resin and 12B4-Resin Followed by Western Imaging with 3D6, 8E5, and 2H3.

FIGS. 6A and B: 7pA2 condition media immunoprecipitated with heparin Sepharose, 8E5-resin and 12B4 resin followed by Western blot imaging with anti-Abeta and anti-APP antibodies.

FIG. 7. Amino terminal sequence results from 8E5 immunoaffinity purification of 7PA2 CM (SEQ ID NOS:10 and 1, respectively).

DEFINITIONS

Figure 1:
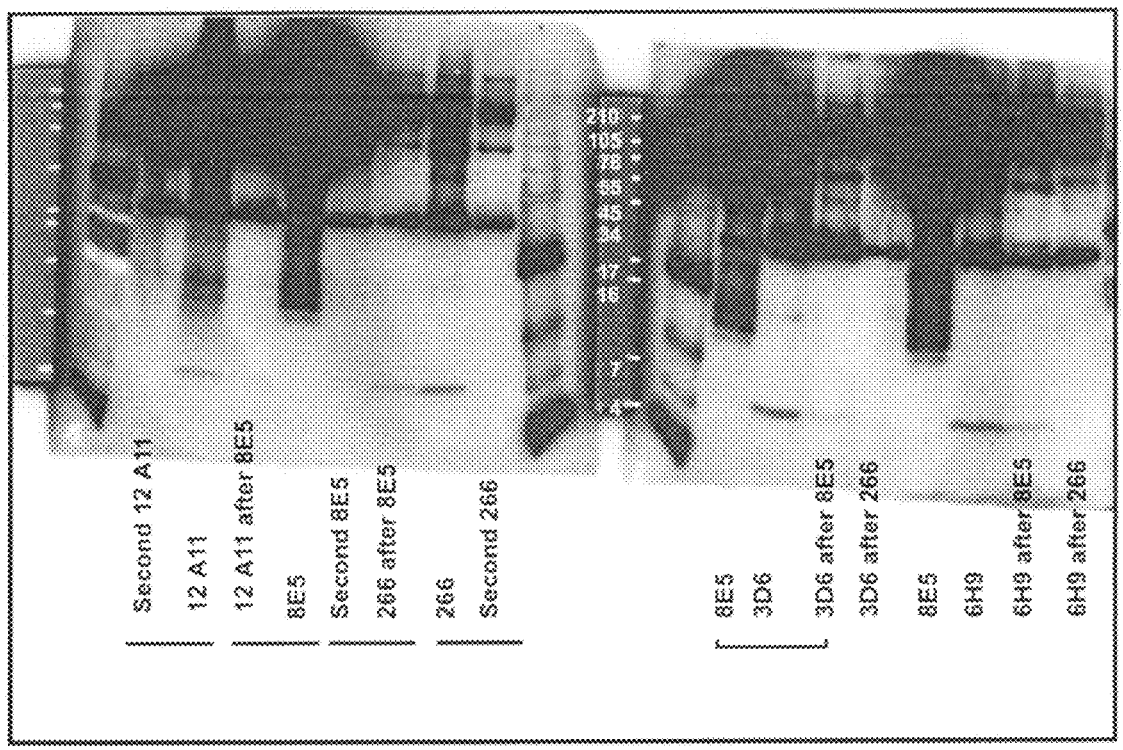
FIG. 1. Immunoprecipitation (IP) and Western of PDAPP Mouse Brain with Anti-Abeta and Anti-APP Antibodies.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

The term "all-D" refers to peptides having ≧75%, ≧80%, ≧85%, ≧90%, ≧95%, and 100% D-configuration amino acids.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

Therapeutic agents of the invention are typically substantially pure from undesired comtaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained. Therapeutic agents of the invention may alleviate the symptoms of, prevent, effect prophylaxis of, or treat a disease associated with amyloid deposits.

Specific binding between two entities means the entities have a mutual affinity for each other that is at least 10-, 100- or 100-fold greater than the affinity of either entity for a control, such as unrelated antigen or antibody to a different antigen. The mutual affinity of the two entities for each other is usually at least $10^7$, $10^8$, $10^9$ $M^{-1}$, or $10^{10}$ $M^{-1}$. Affinities greater than $10^8$ $M^{-1}$ are preferred. Specific binding of a polyclonal antibody to an epitope within Aβ means the antibodies in the polyclonal antibody population specifically bind to one epitope of Aβ without binding to other epitopes of Aβ (change to conform).

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Separate chains include Nanobody antibodies (i.e., the isolated VH fragment of the heavy chain of antibodies from camels or llamas, optionally humanized). Isolated VH fragments can also be obtained from other sources, such as human antibodies. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (19920

Disaggregated Aβ or fragments thereof means monomeric peptide units. Disaggregated Aβ or fragments thereof are generally soluble, and are capable of self-aggregating to form soluble oligomers. Oligomers of Aβ and fragments thereof are usually soluble and exist predominantly as alpha-helices or random coils. One method to prepare monomeric Aβ is to dissolve lyophilized peptide in neat DMSO with sonication. The resulting solution is centrifuged to remove any insoluble particulates. Aggregated Aβ or fragments thereof, means oligomers of Aβ or immunogenic fragments thereof in which the monomeric units are held together by noncovalent bonds and associate into insoluble beta-sheet assemblies. Aggregated Aβ or fragments thereof, means also means fibrillar polymers. Fibrils are usually insoluble.

An "antigen" is an entity to which an antibody specifically binds.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.*, 170, 1110-19 (1994)), by antigen-dependent killing (cytotoxic T lymphocyte assay, Tigges et al., *J. Immmunol.*, 156, 3901-3910) or by cytokine secretion.

The term "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays (see Burke, supra; Tigges, supra). The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "patient" includes human and other mammalian subjects that receive either prophylactic or therapeutic treatment.

Competition between antibodies is determined by an assay in which the immunoglobulin under test inhibits specific binding of a reference antibody to a common antigen, such as Aβ. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology,* 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, *"Antibodies, A Laboratory Manual,"* Cold Spring Harbor Press (1988)); solid phase direct label RIA using I-125 label (see Morel et al., Molec. Immunol. 25(1):7-15 (1988)); solid phase direct biotin-avidin EIA (Cheung et al., *Virology,* 176:546-552 (1990)); and direct labeled RIA (Moldenhauer et al., *Scand. J. Immunol.,* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

Long-term potentiation (LTP) is a kind of "increased sensitivity" that develops with repeated sending and receiving of a message across a synapse.

Compositions or methods "comprising" one or more recited elements may include other elements not specifically recited. For example, a composition that comprises Aβ peptide encompasses both an isolated Aβ peptide and Aβ peptide as a component of a larger polypeptide sequence.

Unless otherwise apparent from the context, each embodiment, element, step or feature of the invention can be used in combination with any other.

DETAILED DESCRIPTION OF THE INVENTION

I. General

The application is premised in part on the identification of novel neuroactive fragments of human amyloid precursor protein (APP). The fragments include sequence from the Aβ region of APP but also extend upstream. The fragments are typically soluble in aqueous solution and can be isolated in the same molecular weight fraction as what have previously been classified as "oligomers" of Aβ. Most bands are ~10 kDa and above and do not correspond with the expected molecular weight of an Aβ dimer or trimer. Because of the similarity in molecular weight to oligomers of Aβ and crossreactivity to Aβ antibodies, the present fragments are sometimes known as fauxligomers. The fragments and subfragments thereof can be used as immunogens in methods of immunotherapy to treat Alzheimer's and other amyloidogenic diseases characterized by deposits of Aβ in the brain. Antibodies to the part of the fragment upstream from APP or the interface between Aβ and the upstream sequence can also be used in such therapeutic method. The fragments are also useful as markers, which can be detected for diagnosis or prognosis of disease or for screening agents. Agents are screened for capacity to reduce the level of such fragments in transgenic animal models of Alzheimer's disease.

II. APP and Aβ

$APP^{695}$, $APP^{751}$, and $APP^{770}$ refer, respectively, to the 695, 751, and 770 amino acid residue long polypeptides encoded by the human APP gene. See Kang et al., *Nature,* 325, 773 (1987); Ponte et al., *Nature,* 331, 525 (1988); and Kitaguchi et al., *Nature,* 331, 530 (1988). Amino acids within the human amyloid precursor protein (APP) are assigned numbers according to the sequence of the APP695 isoform (SEQ ID NO:2) unless otherwise indicated. Amino acids in APP from species other than human are numbered as for corresponding amino acids in human APP when the sequences are maximally aligned. Guinea pig APP differs from human APP at several position including positions 548 and 551.

Amyloid precursor protein can be processed through at least two pathways, one of which leads to production of Aβ. Production of Aβ is initiated by cleavage by beta-secretase between residues 596 and 597 of APP to form the N-terminus of Aβ and an amino terminal fragment known as ATF-βAPP (see U.S. Pat. No. 6,018,024). The C-terminus of Aβ is formed by cleavage by gamma secretase within the transmembrane region of APP. In an alternative, presumably non-pathogenic pathway, APP is cleaved within the Aβ sequence by α-secretase, which generates another large secreted N-terminal fragment and a C-terminal fragment.

Aβ, also known as β-amyloid peptide, or A4 peptide (see U.S. Pat. No. 4,666,829; Glenner & Wong, *Biochem. Biophys. Res. Commun.,* 120, 1131 (1984)), is a peptide of 39-43 amino acids, which is the principal component of characteristic plaques of Alzheimer's disease. Aβ has several natural occurring forms. The natural human forms of Aβ are referred to as Aβ39, Aβ40, Aβ41, Aβ42 and Aβ43. The sequences of these peptides and their relationship to the APP precursor are illustrated by FIG. 1 of Hardy et al., TINS 20, 155-158 (1997). For example, Aβ42 has the sequence:

```
                                           (SEQ ID NO:1)
H2N-Asp-Ala-Glu-Phe-Arg-His-Asp-Ser-Gly-Tyr-Glu-

Val-His-His-Gln-Lys-Leu-Val-Phe-Phe-Ala-Glu-Asp-

Val-Gly-Ser-Asn-Lys-Gly-Ala-Ile-Ile-Gly-Leu-Met-

Val-Gly-Gly-Val-Val-Ile-Ala-OH.
```

Terms such as Aβ39, Aβ40, Aβ41, Aβ42 and Aβ43 refer to an Aβ peptide containing amino acid residues 1-39, 1-40, 1-41, 1-42 and 1-43, respectively. Aβ41, Aβ40 and Aβ39 differ from Aβ42 by the omission of Ala, Ala-Ile, and Ala-Ile-Val respectively from the C-terminal end. Aβ43 differs from Aβ42 by the presence of a threonine residue at the C-terminus. Likewise, the term APP516-638 means an APP polypeptide consisting of residues 516 to 638 of APP as defined below, preferably, the natural human sequence of Kang. Likewise, the term APP536-638 means a fragment of APP consisting of residues 536-638. The APP sequence can be the human sequence of SEQ ID NO:1 or variants thereof as discussed in more detail below. If a variant is included the variant is preferably a natural allelic variant, particularly a natural variant known or suspected to be associated with Alzheimer's disease, such as one of the variants at codon 642 (695 numbering). Such APP polypeptides can be linked to heterologous peptides to APP, e.g., to assist with purification or to induce an immune response. Analogous nomenclature is used to describe other APP fragments, such as APP516-639 or APP536-639.

Unless otherwise apparent from the context reference to APP or Aβ includes the natural human amino acid sequence of Kang, supra (SEQ ID NO:2) as well as analogs including allelic, species and induced variants. Analogs of APP or Aβ induce antibodies that specifically bind with a natural human APP or Aβ peptide respectively. Analogs of APP or Aβ typically show at least 90% sequence identity to the natural human APP or Aβ sequence over the entire length of the analog. Amino acids substitutions are often conservative substitutions. Examples of known allelic variants in APP include Glu590Asp (*), Lys/Met595,596Asn/Leu (*, Swedish), Ala598Thr, His602Arg (*), Asp603Asn (*), Ala617Gly, Glu618Gly (*), Glu618Gln, Glu618Lys, Asp619Asn (*), Ala638Thr (*), Ala638Val, Thr639Ile (*), Thr639Ala (*), Val640Met (*), Val640Met (*), Ile641Val(*), Ile641Thr(*), Val642Phe(*), Val642Gly(*), Val 642Ile(*), Val642Leu(*), and Leu648Pro(*) (*=known or suspected to be associated with Alzheimer's disease) (see Alzheimer's Research Forum APP Mutations Directory, Jul. 24, 2001 update). Typically fragments contain no more than 5 substitutions relative to the natural human sequence.

Some analogs of APP or Aβ or Aβ fragments also include unnatural amino acids or modifications of N or C terminal amino acids at one, two, five, ten or even all positions. For example, the natural aspartic acid residue at position 1 and/or 7 of Aβ can be replaced with iso-aspartic acid. Examples of unnatural amino acids are D, alpha, alpha-disubstituted amino acids, N-alkyl amino acids, lactic acid, 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, omega-N-methylarginine, β-alanine, ornithine, norleucine, norvaline, hydroxproline, thyroxine, gamma-amino butyric acid, homoserine, citrulline, and isoaspartic acid. Some therapeutic agents of the invention are all-D peptides. Fragments and analogs can be screened for prophylactic or therapeutic efficacy in transgenic animal models in comparison with untreated or placebo controls as described below.

APP, Aβ, and their fragments, and analogs can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., *Molecular Cloning: A Laboratory Manual* (C.S.H.P. Press, NY 2d ed., 1989). Some forms of Aβ peptide are also available commercially (e.g., American Peptides Company, Inc., Sunnyvale, Calif. and California Peptide Research, Inc. Napa, Calif.)

III. Fragments of the Invention

The invention provides a novel class of fragments of APP conferring neurotoxicity. The fragments are optionally soluble in Tris/NaCl buffer of neutral pH, in the absence of detergent, e.g., in the concentration ranges shown in FIGS. 8 and/or 9A and 9B. The fragments have been found in transgenic animal models, primary cortical cells, and cell lines transfected with nucleic acids encoding APP. Fragments of similar molecular weight can also be found in Alzheimer's patients. The fragments are also provided in isolated form. The fragments preferably exhibit toxicity against human cortical neurons e.g., under the conditions described in the Examples. The fragments are characterized by presence of sequence upstream of the Aβ region of APP. The upstream sequence is usually at least 25 contiguous amino acids between positions 551 and 595 or 596 of APP. Some fragments include each residue between position 551 and 595 or 596 of APP. The fragments have a length of about 50-200 amino acids, and preferably 80-100 amino acids, or 85-95 amino acids. Thus, the fragments lack a substantial portion of the N-terminus of APP (e.g., at least from about 100 to about 400). Some fragments do not extend all the way to the C-terminus of APP and lack specific binding to C-terminal antibodies of APP, such as 13G8 raised to a fragment of APP consisting of residues 676-695. Some fragments include sequence from the Aβ region of APP and additional sequence upstream thereof. Some such fragments comprise first and second segments, a first segment from Aβ, and a second segment upstream of Aβ, the first and second segments forming a contiguous fragment of APP. For example, some fragments comprise a segment of APP beginning at residue 548 or 551 and extending to residue 636, 637, 638 or 639 of APP (the C-termini of Aβ40, Aβ41, Aβ42 and Aβ43 respectively). A preferred fragment consists of residues from position 548 to 638 of APP. Some fragments include residues 516-525 and/or 536-545 of APP. Some fragments begin at a residue between 444 and 550 and end at a residue selected from the group consisting of 636, 637, 638 or 639 of APP. Some fragments being at a residue between 444 and 550 and end at a residue between positions 636 and 675 of APP. Some fragments begin at a residue between positions 444 and 550 and end at position between residue 595 or 596 and 675 of APP. Some fragments begin at residue 535 or 536 and end at a residue selected from the group consisting of residues 634, 635, 636, 637, 638, 639, 640, 641, or 642 of APP. Some fragments begin at residue 516 and end at residue 634, 635, 636, 637, 638, 639, 640, 641, or 642 of APP. Preferred fragments include APP56-638, APP516-639, APP536-638 and APP536-639.

Some fragments are further characterized by their capacity to specifically bind monoclonal antibodies having epitopes in APP upstream to the Aβ region. Binding can be detected, for example, using antibodies linked to activated NHS-Sepharose® resin. These antibodies include 8E5 (raised to APP444-592) and 18B10 (raised to APP 530-580). Some fragments also specifically bind to certain antibodies having epitopes within Aβ (see examples).

For therapeutic purposes, subfragments of the fragments described above can be administered. A subfragment usually comprises or consists of at least 4, 5, 7, 10, 15 or 25 contiguous residues between positions 551 and 595 or 596 of human APP, but can extend beyond these coordinates. Optionally, subfragments of APP consist of 4-25 residues of APP, preferably 5-15, or 5-10 residues of APP between positions 516 and 596 or between positions 536 and 596.

IV. Antibodies of the Invention

The invention provides antibodies specifically binding to an epitope within residues 444-595, 444-596 or 444-592 of human amyloid precursor protein. Some antibodies are characterized by capacity to specifically bind human APP without specifically binding to guinea pig APP, which differs from human APP at positions 548 and 551. Some antibodies specifically bind to an epitope within residues 540-595 or 540-596 of human APP. Some antibodies specifically bind to an epitope within residues 545-595 or 545-596 of human APP. Some antibodies specifically bind to an epitope within residues 545-555 of human APP. Some antibodies specifically bind to an epitope within residues 530-580 of human APP.

Two exemplary antibodies are 8E5 and 18B10. The antibodies are each mouse monoclonals produced by hybridomas designated 8E5 and 18B10 respectively. Other antibodies referred to herein are likewise mouse antibodies produced from hybridomas of the same name, unless otherwise noted.

8E5 was raised to a fragment of human APP consisting of residues 444-595. However, 8E5 does not bind guinea pig APP, which differs from human APP at residues 548 and 551, thereby localizing the epitope to a segment including or close to these residues. of APP. 18B10 was raised to a fragment of APP consisting of residues 530-580. The invention further provides antibodies that compete with 8E5 or 18B10 for specific binding to human APP. Competition between antibodies indicates that they bind to the same epitope or an epitopes sufficiently proximal for binding of the antibodies to interfere with specific binding of one another to human APP.

The invention also provides antibodies that specifically bind to the junction or interface between Aβ and upstream sequences without specifically binding to Aβ or upstream sequence alone. The epitope of such antibodies includes at least one residue of APP from the Aβ region and at least one residue upstream of the Aβ region.

The invention further provides amino acids that are end-specific for the N-terminus of the novel fragments of the invention. The N-terminus of such fragments can be between codons 530 and 560 of human APP, or between residues 540 and 551 or 535-555 of human APP. Some end-specific antibodies are end-specific for the N-terminus of the fragment APP516-638 or APP516-639 or the fragment APP536-638 or APP536-639. End-specific means that the antibody specifically binds to the N-terminus of such a fragment without specifically binding to full-length APP (which includes the fragment as an internal sequence).

Antibodies can be polyclonal or monoclonal. Polyclonal sera typically contain mixed populations of antibodies specifically binding to several epitopes along the length of APP. However, polyclonal sera can be specific to a particular segment of APP, such as APP551-595 or 551-596. Preferred antibodies are chimeric, humanized (see Queen et al., *Proc. Natl. Acad. Sci. USA* 86:10029-10033 (1989) and WO 90/07861, U.S. Pat. Nos. 5,693,762, 5,693,761, 5,585,089, 5,530,101 and Winter, U.S. Pat. No. 5,225,539), or human (Lonberg et al., WO93/12227 (1993); U.S. Pat. Nos. 5,877, 397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991)) EP1481008, Bleck, Bioprocessing Journal 1 (September/October 2005), US2004132066, US2005008625, WO2004072266, WO2005065348, WO2005069970, and WO2006055778. Humanized or chimeric forms of 8E5, or 18B10 are preferred. Human isotype IgG1, IgG2, IgG3 or IgG4 can be used for humanized or chimeric antibodies. Human isotype IgG1 has the highest affinity of human isotypes for the FcRI receptor on phagocytic cells. Some antibodies specifically bind to APP with a binding affinity greater than or equal to about $10^7$, $10^8$, $10^9$, or $10^{10}$ M$^{-1}$.

V. Methods of Screening

The novel fragments of the invention are useful in screening agents for pharmacological activity useful for treating Alzheimer's and other diseases characterized by deposits of Aβ in the brain. The screening is usually performed in a transgenic animal model of Alzheimer's disease or cells expressing APP. The transgenic animal model expresses APP and process it to Aβ and other fragments, one or more of which are fragments of the invention. Likewise, cells expressing APP process it to Aβ and one or more fragments of the invention. The methods entail contacting a transgenic animal model or cell with an agent being tested and measuring a level of a fragment of the invention in the brain of the animal or in cell culture medium. The fragment can be extracted from the brain in a soluble fraction as described in the Examples. The level of the fragment in the brain or cell culture medium is compared with the corresponding level of the fragment in a control transgenic animal or cell, which has not been treated with the agent being screened. A reduction in the level of the fragment of the invention beyond the typical margin of measurement error is an indication that the agent being screened has a pharmacological activity useful for treating Alzheimer's and other diseases characterized by deposits of Aβ in the brain.

Transgenic animal models generally have a genome comprising a nucleic acid encoding APP and one or more regulatory elements in operable linkage thereto, such that the APP can be processed to Aβ and other fragments, and the animal is disposed to develop one or more characteristic of Alzheimer's diseases. Such models include, for example, mice bearing a 717 (APP770 numbering) mutation of APP described by Games et al., supra, and mice bearing a 670/671 (APP770 numbering) Swedish mutation of APP such as described by McConlogue et al., U.S. Pat. No. 5,612,486 and Hsiao et al., *Science*, 274, 99 (1996); Staufenbiel et al., *Proc. Natl. Acad. Sci. USA*, 94:13287-13292 (1997); Sturchler-Pierrat et al., *Proc. Natl. Acad. Sci. USA*, 94:13287-13292 (1997); Borchelt et al., *Neuron*, 19:939-945 (1997)); Richards et al., J. Neurosci. 23:8989-9003, 2003; Cheng, Nat Med. 10(11): 1190-2, 2004 Hwang et al., Exp Neurol. 2004 March. Mutations of APP suitable for inclusion in transgenic animals include conversion of the wild-type Val717 (APP770 numbering) codon to a codon for Ile, Phe, Gly, Tyr, Leu, Ala, Pro, Trp, Met, Ser, Thr, Asn, or Gln. A preferred substitution for Val717 is Phe. Another suitable mutation is the arctic mutation E693G (APP 770 numbering). The PSAPP mouse, which has both amyloid precursor protein and presenilin transgenes, is described by Takeuchi et al., American Journal of Pathology. 2000;157:331-339. A triple transgenic mouse having amyloid precursor protein, presenilin and tau transgenes is described by LaFerla, (2003), Neuron 39, 409-421. Another useful transgenic mouse has both APP and TGF-beta transgenes. Protein encoding sequences in transgenes are in operable linkage with one or more suitable regulatory elements for neural expression. Such elements include the PDGF, prion protein and Thy-1 promoters. Another useful transgenic mouse has an APP transgene with both a Swedish and 717 mutation. Another useful transgenic mouse has an APP transgene with an arctic mutation (E693G).

Suitable cells include cells naturally expressing detectable amounts of APP and cells transfected with a nucleic acid encoding APP in operable linkage to at least one regulatory sequence to ensure its expression. Suitable cell lines include human and animal cell lines, such as 293 human kidney cell line, human neuroglioma cell lines, human HeLa cells, primary endothelial cells (e.g., HUVEC cells), primary human fibroblasts or lymphoblasts (including endogenous cells derived from patients with APP mutations), primary human mixed brain cells (including neurons, astrocytes and neuroglia), Chinese hamster ovary (CHO) cells, and the like.

The invention provides further methods of screening in which a fragment of the invention is contacted with neuronal cells in vitro, and an agent is screened for a protective effect relative to control cells of the same type not treated with the agent. The cells are a primary culture of cortical cells, preferably human cortical cells. Neurotoxicity can be measured as an $LD_{50}$ value, effect on long term potentiation, by alamar blue staining or effect on branch number or distance as described in the Examples.

The agents to be screened for activity in such method can reduce the concentration of soluble fragment by a variety of mechanisms. One mechanism is through inhibition of enzymes responsible for generating the fragment. These enzymes can include gamma secretase for generation of the C-terminus and an enzyme as yet unidentified for generation of the N-terminus. Thus agents to be screened include protease inhibitors, including such inhibitors as have already been identified for inhibiting beta or gamma secretase. Other agents can be obtained from natural sources, such as, e.g., marine microorganisms, algae, plants, and fungi. Alternatively, compounds can be from combinatorial libraries of agents, including peptides or small molecules, or from existing repertoires of chemical compounds synthesized in industry, e.g., by the chemical, pharmaceutical, environmental, agricultural, marine, cosmeceutical, drug, and biotechnological industries. Compounds can include, e.g., pharmaceuticals, therapeutics, environmental, agricultural, or industrial agents, pollutants, cosmeceuticals, drugs, organic compounds, lipids, glucocorticoids, antibiotics, peptides, proteins, sugars, carbohydrates, and chimeric molecules.

Random libraries of peptides or other compounds can also be screened. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, W0 91/18980.

VI. Conjugates

Peptide immunogens can be linked to a suitable carrier molecule to form a conjugate which helps elicit an immune response comprising antibodies to the peptide. A single agent can be linked to a single carrier, multiple copies of an agent can be linked to multiple copies of a carrier, which are in turn linked to each other, multiple copies of an agent can be linked to a single copy of a carrier, or a single copy of an agent can be linked to multiple copies of a carrier, or different carriers. Suitable carriers include serum albumins, keyhole limpet hemocyanin, immunoglobulin molecules, Qβ (WO 04/016282), thyroglobulin, ovalbumin, tetanus toxoid, or a toxoid from other pathogenic bacteria, such as diphtheria, E. coli, cholera, or H. pylori, or an attenuated toxin derivative. T cell epitopes are also suitable carrier molecules. Other suitable carriers include promiscuous T helper cell epitopes which are derived from hepatitis B virus, Bordetella pertussis, Clostridium tetani, Pertusaria trachythallina, Escherichia coli, Chlamydia trachomatis, Diphtheria, Plasmodium falciparum, and Schistosoma mansoni (see U.S. Pat. No. 6,906,169, US 2003-0068325, and WO/2002/096350). Other carriers are T helper cell epitopes derived from tetanus toxin, pertussis toxin, diphtheria toxin, measles virus F protein, hepatitis B virus surface antigen, Chlamydia trachomatis major outer membrane protein, Plasmodium falciparum circumsporozoite, Schistosoma mansoni triose phosphate isomerase, or Escherichia coil TraT (see WO 01/42306).

Some conjugates can be formed by linking agents of the invention to an immunostimulatory polymer molecule (e.g., tripalmitoyl-S-glycerine cysteine ($Pam_3Cys$), mannan (a manose polymer), or glucan (a beta 1→2 polymer)), cytokines (e.g., IL-1, IL-1 alpha and beta peptides, IL-2, gamma-INF, IL-10, GM-CSF), and chemokines (e.g., MIP1alpha and beta, and RANTES). Immunogenic agents can also be linked to peptides that enhance transport across tissues, as described in O'Mahony, WO 97/17613 and WO 97/17614. Immunogens may be linked to the carries with or with out spacers amino acids (e.g., gly-gly).

Some conjugates can be formed by linking agents of the invention to at least one T cell epitope. Some T cell epitopes are promiscuous whereas other T cell epitopes are universal. Promiscuous T cell epitopes are capable of enhancing the induction of T cell immunity in a wide variety of subjects displaying various HLA types. In contrast to promiscuous T cell epitopes, universal T cell epitopes are capable of enhancing the induction of T cell immunity in a large percentage, e.g., at least 75%, of subjects displaying various HLA molecules encoded by different HLA-DR alleles.

A large number of naturally occurring T-cell epitopes exist, such as, tetanus toxoid (e.g., the P2 and P30 epitopes), Hepatitis B surface antigen, pertussis, toxoid, measles virus F protein, Chlamydia trachomitis major outer membrane protein, diphtheria toxoid, Plasmodium falciparum circumsporozite T, Plasmodium falciparum CS antigen, Schistosoma mansoni triose phosphate isomersae, Escherichia coli TraT, and Influenza virus hemagluttinin (HA). The immunogenic peptides of the invention can also be conjugated to the T-cell epitopes described in Sinigaglia F. et al., Nature, 336: 778-780 (1988); Chicz R. M. et al., J. Exp. Med., 178:27-47 (1993); Hammer J. et al., Cell 74:197-203 (1993); Falk K. et al., Immunogenetics, 39:230-242 (1994); WO 98/23635; and, Southwood S. et al. J. Immunology, 160:3363-3373 (1998) (each of which is incorporated herein by reference for all purposes). Further examples include:

```
Influenza Hemagluttinin:
HA307-319

Malaria CS: T3 epitope
EKKIAKMEKASSVFNV                      (SEQ ID NO:3)

Hepatitis B surface antigen:
HBsAg19-28 FFLLTRILTI                 (SEQ ID NO:4)

Heat Shock Protein 65:
hsp65153-171 DQSIGDLIAEAMDKVGNEG      (SEQ ID NO:5)

bacille Calmette-Guerin
QVHFQPLPPAVVKL                        (SEQ ID NO:6)

Tetanus toxoid:
TT830-844 QYIKANSKFIGITEL             (SEQ ID NO:7)

Tetanus toxoid:
TT947-967 FNNFTVSFWLRVPKVSASHLE       (SEQ ID NO:8)

HIV gp120 T1:
KQIINMWQEVGKAMYA.                     (SEQ ID NO:9)
```

Alternatively, the conjugates can be formed by linking agents of the invention to at least one artificial T-cell epitope capable of binding a large proportion of MHC Class II molecules, such as the pan DR epitope ("PADRE"). PADRE is described in U.S. Pat. No. 5,736,141, WO 95/07707, and Alexander J et al., Immunity, 1:751-761 (1994) (each of which is incorporated herein by reference for all purposes). A preferred PADRE peptide is AKXVAAWTLKAAA (SEQ ID NO: 11), wherein X is preferably cyclohexylalanine tyrosine or phenylalanine, with cyclohexylalanine being most preferred.

Immunogenic agents can be linked to carriers by chemical crosslinking. Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by *Immun. Rev.* 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Immunogenicity can be improved through the addition of spacer residues (e.g., Gly-Gly) between the $T_h$ epitope and the peptide immunogen of the invention. In addition to physically separating the $T_h$ epitope from the B cell epitope (i.e., the peptide immunogen), the glycine residues can disrupt any artificial secondary structures created by the joining of the $T_h$ epitope with the peptide immunogen, and thereby eliminate interference between the T and/or B cell responses. The conformational separation between the helper epitope and the antibody eliciting domain thus permits more efficient interactions between the presented immunogen and the appropriate $T_h$ and B cells.

To enhance the induction of T cell immunity in a large percentage of subjects displaying various HLA types to an agent of the present invention, a mixture of conjugates with different $T_h$ cell epitopes can be prepared. The mixture may contain a mixture of at least two conjugates with different $T_h$ cell epitopes, a mixture of at least three conjugates with different $T_h$ cell epitopes, or a mixture of at least four conjugates with different $T_h$ cell epitopes. The mixture may be administered with an adjuvant.

Immunogenic peptides can also be expressed as fusion proteins with carriers (i.e., heterologous peptides). The immunogenic peptide can be linked at its amino terminus, its carboxyl terminus, or both to a carrier. Optionally, multiple repeats of the immunogenic peptide can be present in the fusion protein. Optionally, an immunogenic peptide can be linked to multiple copies of a heterologous peptide, for example, at both the N and C termini of the peptide. Optionally, multiple copies of an immunogenic peptide can be linked to multiple copies of a heterologous peptide. which are linked to each other. Some carrier peptides serve to induce a helper T-cell response against the carrier peptide. The induced helper T-cells in turn induce a B-cell response against the immunogenic peptide linked to the carrier.

Some fusion proteins comprise segments of APP of the invention linked to tetanus toxoid epitopes such as described in U.S. Pat. No. 5,196,512, EP 378,881 and EP 427,347. Some fusion proteins comprise segments of APP of the invention linked to at least one PADRE peptide described in U.S. Pat. No. 5,736,142. Some heterologous peptides are promiscuous T-cell epitopes, while other heterologous peptides are universal T-cell epitopes. In some methods, the agent for administration is simply a single fusion protein with an APP segment of the invention linked to a heterologous segment in linear configuration. The therapeutic agents of the invention can be represented using a formula. For example, in some methods, the agent is multimer of fusion proteins represented by the formula $2^x$, in which x is an integer from 1-5. Preferably x is 1, 2 or 3, with 2 being most preferred. When x is two, such a multimer has four fusion proteins linked in a preferred configuration referred to as MAP4 (see U.S. Pat. No. 5,229,490).

Other examples of carriers are described in WO2004069182. The fragments of APP described in the present application can be used in place of the Aβ fragments linked to conjugates as described in WO2004069182.

The same or similar carrier proteins and methods of linkage can be used for generating immunogens to be used in generation of antibodies against APP or an immunogenic fragment thereof. For example, APP or an immunogenic fragment of APP linked to a carrier can be administered to a laboratory animal in the production of monoclonal antibodies to APP or an immunogenic fragment thereof.

VII. DNA Immunization

Immune responses against APP segments can also be induced by administration of nucleic acids encoding novel fragments of the invention and subfragments thereof, other peptide immunogens, or antibodies and their component chains used for passive immunization. Such nucleic acids can be DNA or RNA. A nucleic acid segment encoding an immunogen or antibody is typically linked to regulatory elements, such as a promoter and enhancer that allow expression of the DNA segment in the intended target cells of a patient. Promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, *Cur. Opin. Genet. Develop.* 3, 102-109 (1993)); adenoviral vectors (see, e.g., Bett et al., *J. Virol.* 67, 5911 (1993)); adeno-associated virus vectors (see, e.g., Zhou et al., *J. Exp. Med.* 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., *J. Virol.* 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., *Human Gene Therapy* 6, 325-333 (1995); Woo et al., WO 94/12629 and Xiao & Brandsma, *Nucleic Acids. Res.* 24, 2630-2622 (1996)).

DNA encoding an immunogen, or a vector containing the same, can be packaged into liposomes. Suitable lipids and related analogs are described by U.S. Pat. Nos. 5,208,036, 5,264,618, 5,279,833 and 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., *J. Micro Encap.* (1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). Such vectors can further include facilitating agents such as bupivacine (U.S. Pat. No. 5,593,970). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see WO 95/05853).

In a further variation, vectors encoding immunogens can be delivered to cells ex vivo, such as cells explanted from an individual patient (e.g., lymphocytes, bone marrow aspirates, tissue biopsy) or universal donor hematopoietic stein cells, followed by reimplantation of the cells into a patient, usually after selection for cells which have incorporated the vector.

VIII. Patients Amenable to Treatment

Patients amenable to treatment include individuals at risk of disease but not showing symptoms, as well as patients presently showing symptoms. Disease subject to treatment include Alzheimer's diseases and other diseases characterized by deposits of Aβ in the brain, such as Down's syndrome and mild cognitive impairment. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are especially useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to the therapeutic agent (e.g., Aβ peptide) over time. If the response falls, a booster dosage is indicated. In the case of potential Down's syndrome patients, treatment can begin antenatally by administering therapeutic agent to the mother or shortly after birth.

IX. Treatment Regimes

In prophylactic applications, pharmaceutical compositions or medicaments comprising agents of the invention (peptides or antibodies) are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. Thus, a regime that at least partly alleviates or inhibits further worsening of symptoms of a patient having or suspected of having the disease treats the patient irrespective whether the patient is completely cured of the disease. In some methods, administration of agent reduces or eliminates myocognitive impairment in patients that have not yet developed characteristic Alzheimer's pathology.

An amount adequate to accomplish therapeutic or prophylactic treatment is defined as a therapeutically- or prophylactically-effective dose. An amount and frequency of administration adequate to accomplish therapeutic or prophylactic treatment is defined as a therapeutically or prophylactically effective regime. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 µg per patient and more usually from 5-500 µg per injection for human administration. Occasionally, a higher dose of 1-2 mg per injection is used. Typically about 10, 20, 50 or 100 µg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for microgram of immunogen. The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at time intervals, such as 6 week intervals. Another regimen consists of an immunization followed by booster injections 1, 2 and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to Aβ in the patient. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 µg to 10 mg, or 30-300 µg DNA per patient. Doses for infectious viral vectors vary from 10-100, or more, virions per dose.

Agents for inducing an immune response can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treatment of amyloidogenic disease. Methods of active and passive immunization using peptides from the Aβ region of APP or antibodies specifically binding to Aβ are described by e.g., U.S. Pat. Nos. 6,866,850, 6,787,637 and 6,818,218. Agents of the invention can also be administered in conjunction with other agents that increase passage of the agents of the invention across the blood-brain barrier.

Immunogenic agents of the invention, such as peptides, are sometimes administered in combination with an adjuvant. A variety of adjuvants can be used in combination with a fragment of APP, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, NY, 1995); U.S. Pat. No. 5,057,540),(Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)). Another adjuvant is CpG ( WO 98/40100). Alternatively, Aβ can be coupled to an adjuvant. However, such coupling should not substantially change the conformation of Aβ so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-A1-D-isoglu-L-Ala-dipalmitoxy propylamide (DTP-DPP) theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (Detox™). Another class of preferred adjuvants is saponin adjuvants, such as Stimulon™ (QS-21, Aquila, Framingham, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. RC529-SE (Corixa Corporation) is also a preferred adjuvant. Optionally, two or more different adjuvants can be used simultaneously. Preferred combinations include alum with MPL, alum with QS-21, MPL with QS-21, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transferal applications.

For suppositories, binders and carriers include, for example, polyalkylene glycols or triglycerides; such suppositories can be formed from mixtures containing the active ingredient in the range of 0.5% to 10%, preferably 1%-2%. Oral fonnulations include excipients, such as phanmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdennal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25, 3521-24 (1995); Cevc et al., *Biochem. Biophys. Acta* 1368, 201-15 (1998)).

EXAMPLES

These examples profile immunoreactive species with the apparent molecular weight of Aβ oligomers from conditioned cell medium and PDAPP brain extracts.

Conditioned medium (CM) from 7PA2 cells was collected after 15 to 18 hours in media without serum from near confluent cells. CM was spun at 1,000 rpm for 30 minutes. CM was transferred to a new tube and evaluated immediately or frozen at $-80°$ C. CM was immunoprecipitated (IP'd) with antibodies coupled to NHS-Sepharose resin, and the corresponding material was detected by Western blot.

The protocol for evaluating soluble, oligomeric species from PDAPP brain tissue was performed as initially described by Lambert, J. Neurochem. 2001, 79:595-605. Briefly, brain tissue was homogenized with a Dounce homogenizer, on ice, in 20 mM Tris, pH 7.6, 137 mM NaCl, with 2% SDS and protease inhibitors (1/10 wt/vol). After a first centrifugation, supernatants containing the soluble species were centrifuged at 200,000 g for 2 hr. The supernatant was aliquoted and stored at $-80°$ C. or was used immediately for immunoprecipitation.

In PDAPP cortical extracts from 12 month old mice, the profile of immunoreactive bands is shown above in FIG. 1. IPs with anti-Aβ and anti-APP antibody resins were preformed followed by a Western blot imaged with 2H3, an anti-Aβ antibody with an epitope to amino acids 4-6 of Aβ. A comparison of the 12A11 IP and the 8E5 IP shows similar immunoreactive profiles in the region between the molecular weight markers 7 kDa to 34 kDa as noted on the Western image. The epitope specificity of the various antibodies used for immunoprecipitation is 3D6 aa 1-5 of AP; 12A11 aa 3-7 of Aβ, 266 aa 16-23 of Aβ, 6H9 aa 19-22 of Aβ, 8E5 aa 444-592 of APP (not epitope mapped).

Figure 2A:
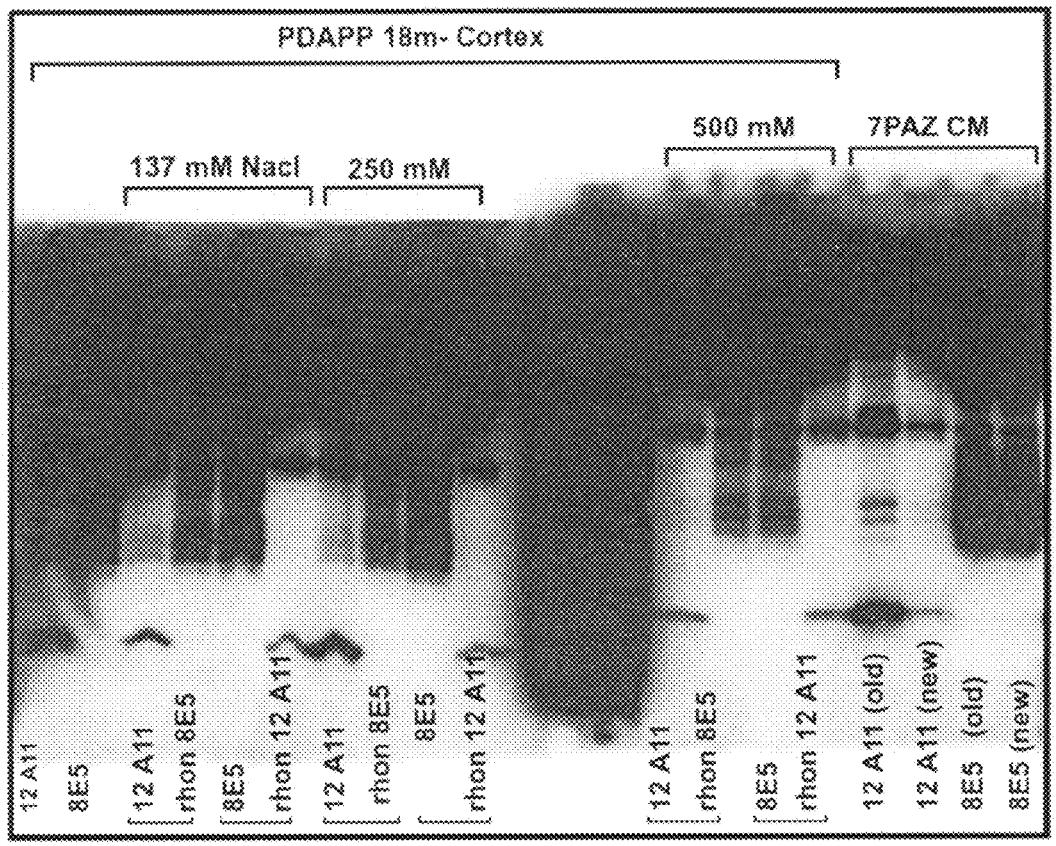
FIGS. 2A and 2B: IP and Western of PDAPP Mouse Brain with Anti-Abeta (12A11) and Anti-APP (8E5) Antibodies After Various Salt Washes of the Immunoprecipitated Brain Preparation. 7PA2 CM Immunoprecipitations For Comparison Purposes.
Figure 2B:
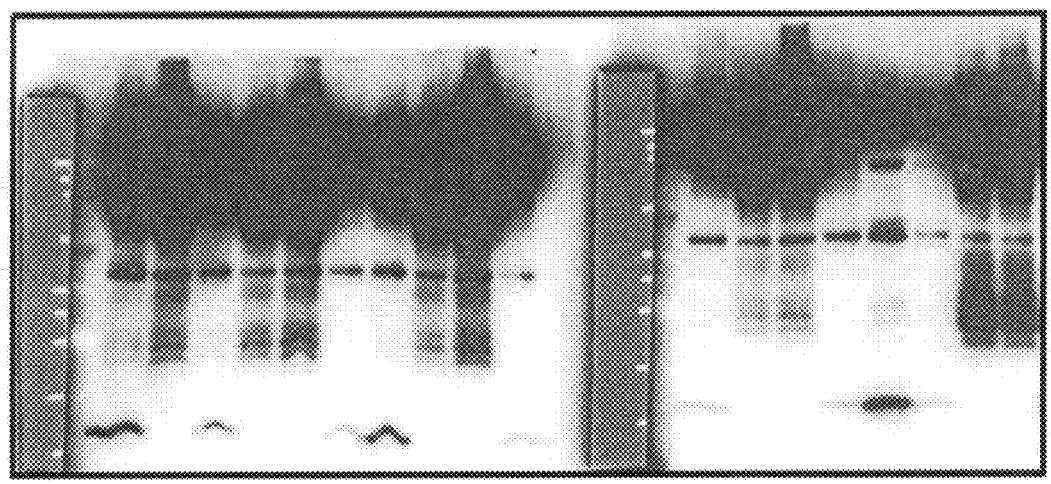

From the above Western images in FIGS. 2A and B, the IP's were washed with various NaCl concentrations. The IP profile of the immunoreactive bands identified from PDAPP brain with 8E5-resin or 12A11-resin does not appear to be different. Sequential immunoprecipitations with both antibodies were also evaluated. The 7PA2 CM immunoreactive bands with 12A11 and 8E5 show very similar profiles to the cortical brain homogenates immunoprecipitated with the 8E5 and 12A11 antibodies except for the monomeric Aβ band (~4 kDa) identified with 12A11 immunoprecipitations. FIGS. 2A and B are darker and lighter exposures of the same blot.

Figure 3:
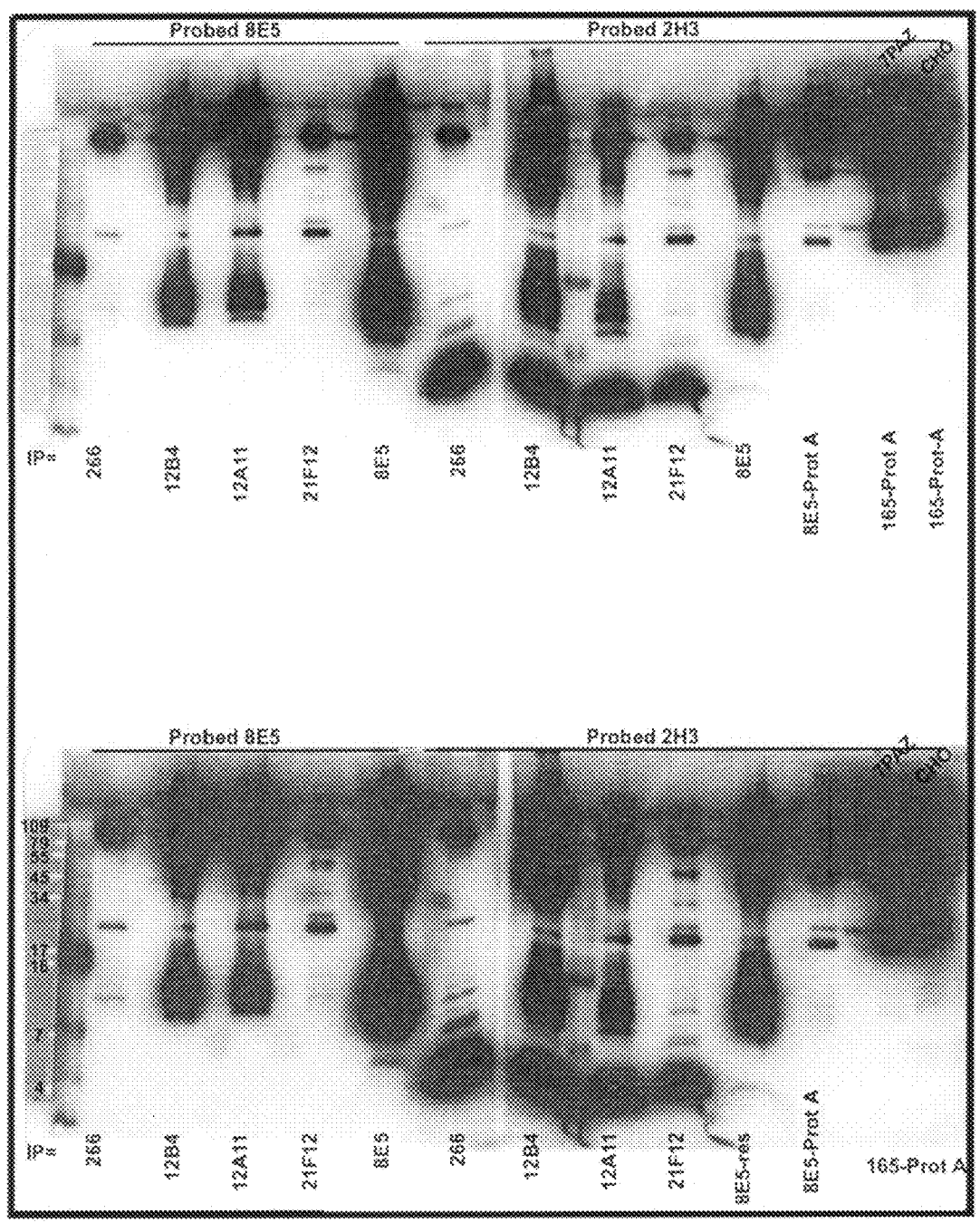
FIG. 3. IP of 7PA2 CM With Anti-Abeta Antibodies and Anti-APP (8E5) Antibody and Imaged with 8E5 or 2H3.

The immunoprecipitated material from anti-Aβ antibodies (266,12B4,12A11, and 21F12) and the anti-APP antibody 8E5 were identified in the Western images probed with either 8E5 or 2H3 (aa 3-7 of Aβ). The immunoreactive profile of 8E5 was very similar to the profiles with anti-Aβ antibodies from the Western imaged with 8E5 or 2H3 except the monomeric Aβ at ~4 kDa detected with anti-Aβ antibody IPs imaged with 2H3 (FIG. 3). Additional antibody specificities used in the blot 12B4 aa3-7 of Aβ, 21F12 aa34-43 of Abeta, 1G55 444-592 of APP, epitope not mapped.

Size exclusion chromatography (SEC) was performed to separate the different Aβ oligomers species, which in turn could be used for a functional assay or for sequencing purposes. The protocol was optimized using conditioned medium from 7PA2 cells. 30 ml CM was concentrated to 2.5 ml with a Vivaspin 5,000 MWCO. Concentrated CM was loaded onto a Superdex 75 preparative grade 16/60 column. 50 mM ammonium acetate buffer was used as the elution buffer and 350 µl fractions were collected into 96 well plates previously blocked overnight with PBS+1% BSA+0.05% NaN$_3$. Fractions were assayed for total Aβ using 266/3D6 ELISA. Pooled fractions were also immunoprecipitated with 12A11-NHS Sepharose resin, and the corresponding material was detected by Western blot. Fractions were assayed by ELISA for total Aβ, showing that no Aβ was detected in fractions 1-31, and a major peak of Aβ was present in fractions 31-81 (lower panel, FIG. 4).

Figure 4:
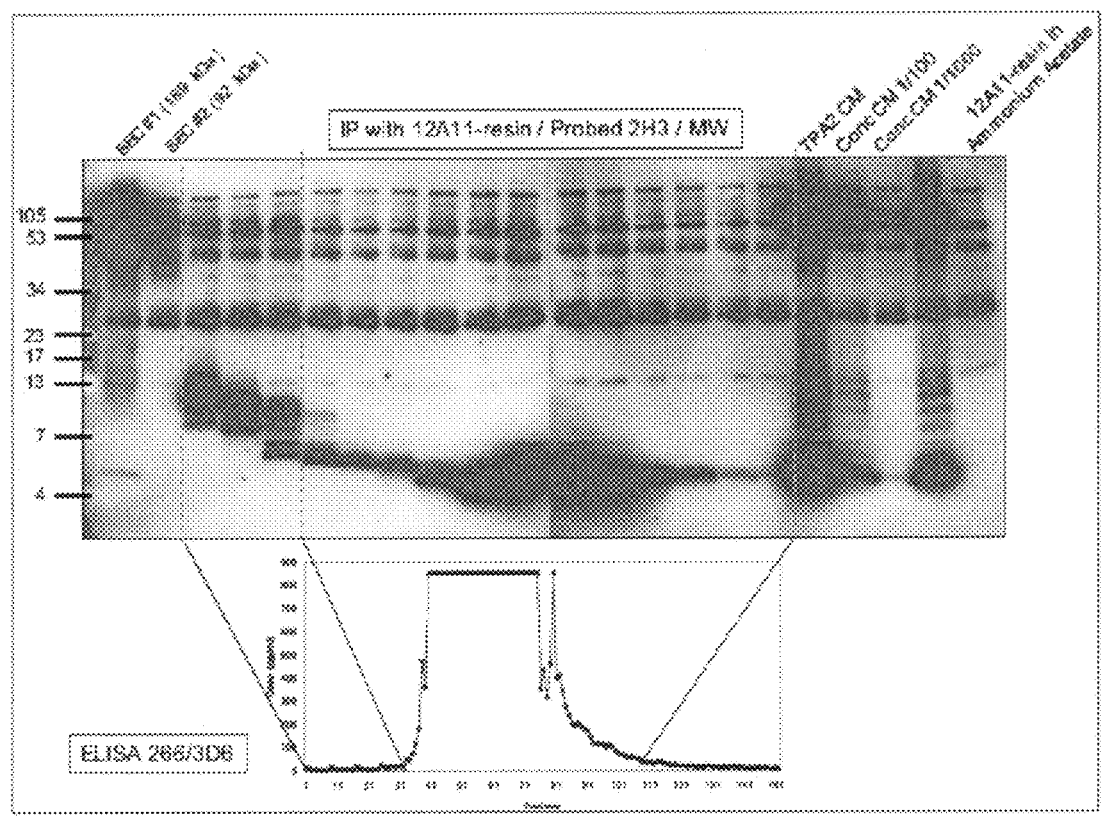
FIG. 4. Size exclusion chromatography (SEC) for 7PA2 CM.

Material immunoprecipitated from the fractions was loaded onto 16% tricine gels, and the corresponding blots probed with the 2H3 antibody (aa 4-6 Aβ 4) (upper panel, FIG. 4).

The SEC procedure described above was utilized followed by the IP/Western procedures discussed in FIG. 4. The pooled fractions (n=10 fractions per pool) are from the SEC plate 3 where the immunoreactivity was identified above in FIG. 4. The pooled fractions from the 7PA2 SEC were immunoprecipitated with 8E5-resin or 12B4-resin followed by imaging with 3D6 (aa 1-5 of Aβ), 8E5 (aa 444-592 of APP), or 2H3 (aa 4-6 of Aβ). The Western images with 3D6 show immunoreactivity of a ~4 kDa band with the 12B4-IP (FIGS. 5A, B, C). The 8E5 Western image shows certain of the immunoreactive bands immunoprecipitated with 8E5-resin or 12B4-resin appear the same. This is followed by the 2H3 Western image. The 2H3 image on the left shows immunoreactive bands with the 8E5 IP above the 7 kDa molecular weight marker. Whereas the 2H3 image with the 12B4 IP shows the same and more immunoreactive bands compared to the 8E5 IP. The 12B4 IP-2H3 image picks up bands in the 7-8 kDa range that 8E5 does not.

FIGS. 6A and B show 7PA2 conditioned media (CM) immunoprecipitated with heparin Sepharose, 8E5-Resin, and 12B4-resin followed by Western blot imaging with anti-Abeta and Anti-APP antibodies. FIG. 6A compare the immunoreactive bands IP'd with 12B4 and 8E5 from 7PA2 CM. Heparin Sepharose binds APP which is another comparator, because it binds APP species. FIG. 6B shows the Western blot imaged with 8E5 and 18G10, two antibodies to similar regions on APP. They show similar immunoreactivity. Also, the 2G3, an Aβ-specific antibody, blot shows reactivity of a 12 kDa band in both the 8E5 and 12B4 IPs.

N-terminal Edman sequencing (10 cycles per sample) of 8E5-immunoprecipitated fragments identified two sequences within APP (as shown in FIGS. 5A,B,C). Based on APP695 numbering, the sequences identified were APP 516-525 and 536-545. Both sequences fall within the 8E5 immunogen which is 444-592. Immunoprecipitation with Aβ42 end-specific antibody 21F12 suggested at least some identified fragments ended at residue 42 of Aβ implying that two of the fragments identified were residues 516-638 and 536-638 of APP. Other fragments likely include other Aβ termination sites, which extend from about residue 634 to 642 of APP.

Based on the data obtained from N-Terminal Edman sequencing, DNA fragments encoding APP 516-638 and APP 536-638 fragments were cloned into a pET21 bacterial expression vector with a 6×Histidine Tag and a Factor Xa protease cleavage site immediate at the N-Terminal of the APP fragments. The APP fragments were transformed into BL21(DE3) chemical competent cells and expressed at 16° C. with routine IPTG induction protocol. The fragments were first purified over an Immobilized Metal Affinity Column (IMAC) to homogeneity via the 6×Histidine affinity tag. To generated recombinant APP 516-638 and APP 536-638 fragments, the IMAC purified fragments were cleaved with Factor Xa overnight at 4° C. Non cleaved fragments, cleaved 6×Histindine tag, and free Factor Xa were removed from the reaction mixture by a tandem IMAC and Factor Xa removal resin. Homogeneous recombinant APP fragments were buffer exchanged into assay buffer for characterization.

Neuronal Morphology was quantified using the Cellomics Neuronal Profiling Bioapplication. The NP Bioapplication performs cell-based measurements integrating information from two-six imaging channels. Typically cells are stained with a Hoechst dye that binds DNA and identifies the nuclear region. Nuclear features such as size shape and intensity are measured.

Neuronal cell bodies and neurites were identified using a monoclonal antibody to tubulin and then stained with a fluorescent-labeled secondary antibody. Neurite features such as neuronal length, branch point average count (BPAC), and branch point average distance from cell body (BPADCB), were automatically calculated by the Bioapplication. BPADCB, one of the more useful readout parameters in the NP Bioapplication, was specifically calculated as the sum of all branch points distances of all neurites from a selected cell body divided by the branch point total count. In addition, BPAC was calculated as the branch point total count divided by neurite count. Cells can be imaged in 24, 96, or 384-well formats using the Cellomics ArrayScan Reader.

Figure 8:
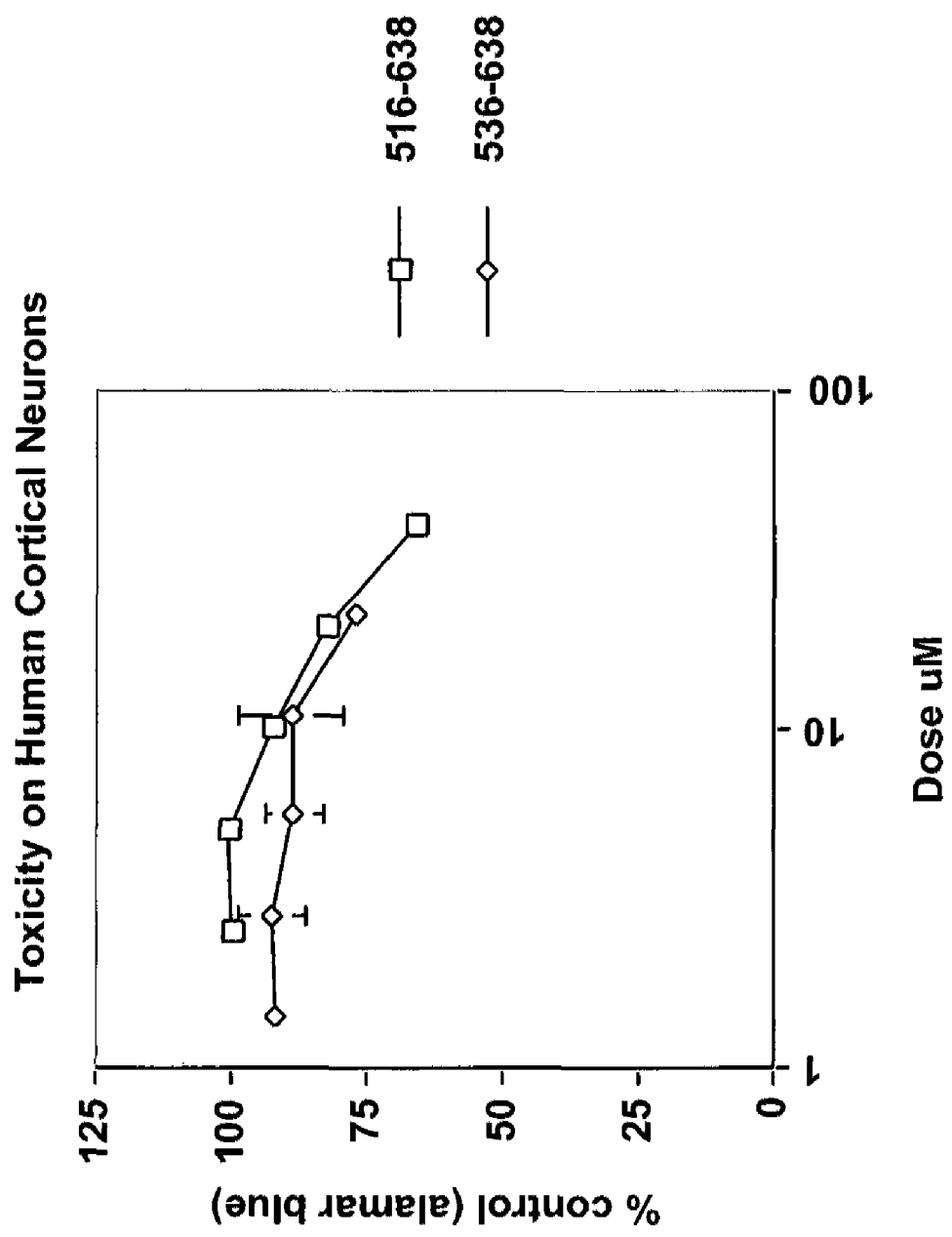
FIG. 8: Toxicity of APP516-638 and APP 536-638 polypeptides on human cortical neurons assayed by alamar blue.

FIG. 8 shows human cortical neurons treated with purified 516 and 536 material for 8 days assayed for metabolic activity using alamarBlue. Treatment with peptides decreased the viability of both 516 and 536 treated cells 20-30% at the highest dose tested (40 uM for 516 and 22 uM for 536).

Figures 9A, 9B:
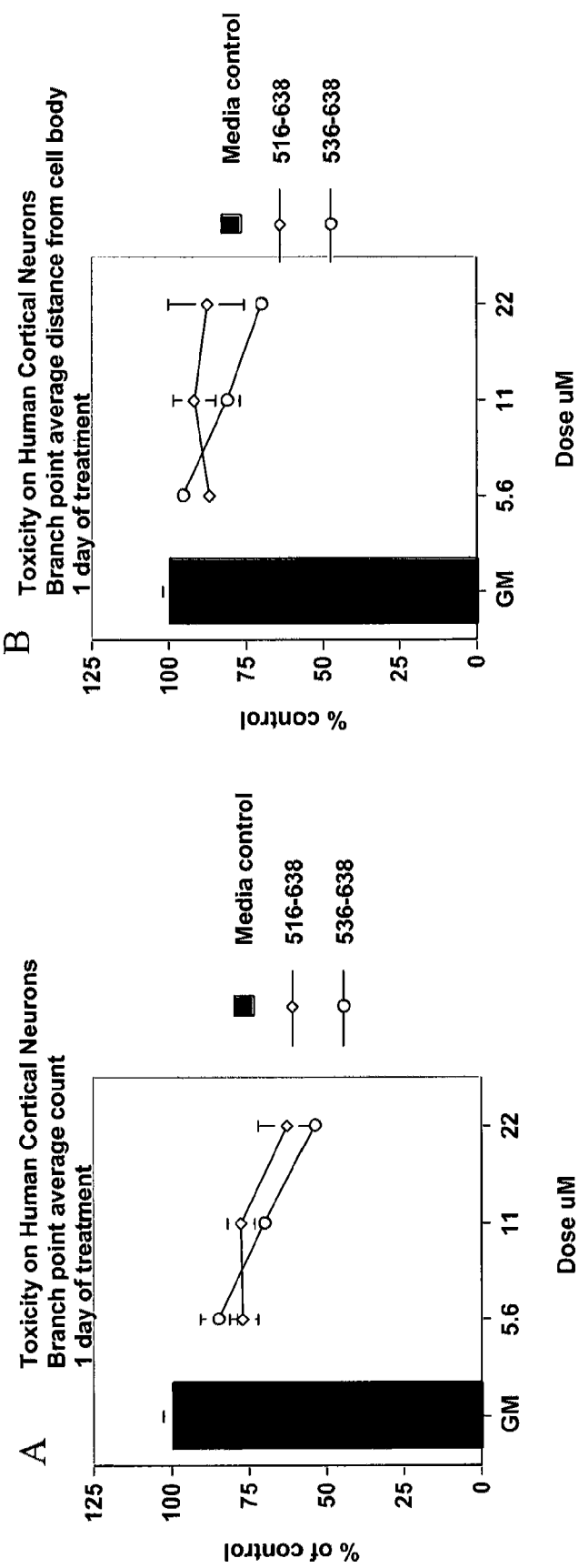
FIGS. 9A and 9B: Toxicity of APP516-638 and APP536-638 peptides on human cortical neurons assayed by branch point average (9A) or average distance of branch point from cell body (9B).

FIGS. 9A and 9B show human cortical neurons treated with purified 516 and 536 material for 1 day, cells were fixed and stained for beta-tubulin to identify cellular morphology. Cells were assayed using Cellomics ArrayScan for neuronal morphology, including the average number of neurite branch points per cell (9A) and for the average distance of branch points from the cell body (9B). Treatment with peptides decreased the both parameters of neuronal morphology as compared to control, indicating early signs of neuronal toxicity.

SEQ ID NO:2
Met Leu Pro Gly Leu Ala Leu Leu Leu Ala Ala
Trp Thr Ala Arg Ala Leu Glu Val Pro Thr Asp Gly
Asn Ala Gly Leu Leu Ala Glu Pro Gln Ile Ala Met

```
Phe Cys Gly Arg Leu Asn Met His Met Asn Val Gln
Asn Gly Lys Trp Asp Ser Asp Pro Ser Gly Thr Lys
Thr Cys Ile Asp Thr Lys Glu Gly Ile Leu Gln Tyr
Cys Gln Glu Val Tyr Pro Glu Leu Gln Ile Thr Asn
Val Val Glu Ala Asn Gln Pro Val Thr Ile Gln Asn
Trp Cys Lys Arg Gly Arg Lys Gln Cys Lys Thr His
Pro His Phe Val Ile Pro Tyr Arg Cys Leu Val Gly
Glu Phe Val Ser Asp Ala Leu Leu Val Pro Asp Lys
Cys Lys Phe Leu His Gln Glu Arg Met Asp Val Cys
Glu Thr His Leu His Trp His Thr Val Ala Lys Glu
Thr Cys Ser Glu Lys Ser Thr Asn Leu His Asp Tyr
Gly Met Leu Leu Pro Cys Gly Ile Asp Lys Phe Arg
Gly Val Glu Phe Val Cys Cys Pro Leu Ala Glu Glu
        180             185             190 Ser Asp Asn Val Asp Ser Ala Asp Ala
Glu Glu Asp Asp Ser Asp Val Trp Trp Gly Gly Ala
Asp Thr Asp Tyr Ala Asp Gly Ser Glu Asp Lys Val
Val Glu Val Ala Glu Glu Glu Val Ala Glu Val
Glu Glu Glu Glu Ala Asp Asp Asp Glu Asp Asp Glu
Asp Gly Asp Glu Val Glu Glu Glu Ala Glu Glu Pro
Tyr Glu Glu Ala Thr Glu Arg Thr Thr Ser Ile Ala
Thr Thr Thr Thr Thr Thr Thr Glu Ser Val Glu Glu
Val Val Arg Val Pro Thr Thr Ala Ala Ser Thr Pro
Asp Ala Val Asp Lys Tyr Leu Glu Thr Pro Gly Asp
Glu Asn Glu His Ala His Phe Gln Lys Ala Lys Glu
Arg Leu Glu Ala Lys His Arg Glu Arg Met Ser Gln
Val Met Arg Glu Trp Glu Glu Ala Glu Arg Gln Ala
Lys Asn Leu Pro Lys Ala Asp Lys Lys Ala Val Ile
Gln His Phe Gln Glu Lys Val Glu Ser Leu Glu Gln
Glu Ala Ala Asn Glu Arg Gln Gln Leu Val Glu Thr
His Met Ala Arg Val Glu Ala Met Leu Asn Asp Arg
Arg Arg Leu Ala Leu Glu Asn Tyr Ile Thr Ala Leu
Gln Ala Val Pro Pro Arg Pro Arg His Val Phe Asn

Met Leu Lys Lys Tyr Val Arg Ala Glu Gln Lys Asp
Arg Gln HisThr Leu Lys His Phe Glu His Val Arg
Met Val Asp Pro Lys Lys Ala Ala Gln Ile Arg Ser
Gln Val Met Thr His Leu Arg Val Ile Tyr Glu Arg
Met Asn Gln Ser Leu Ser Leu Leu Tyr Asn Val Pro
Ala Val Ala Glu Glu Ile Gln Asp Glu Val Asp Glu
Leu Leu Gln Lys Glu Gln Asn Tyr Ser Asp Asp Val
Leu Ala Asn Met Ile Ser Glu Pro Arg Ile Ser Tyr
Gly Asn Asp Ala Leu Met Pro Ser Leu Thr Glu Thr
Lys Thr Thr Val Glu Leu Leu Pro Val Asn Gly Glu
Phe Ser Leu Asp Asp Leu Gln Pro Trp His Ser Phe
Gly Ala Asp Ser Val Pro Ala Asn Thr Glu Asn Glu
Val Glu Pro Val Asp Ala Arg Pro Ala Ala Asp Arg
Gly Leu Thr Thr Arg Pro Gly Ser Gly Leu Thr Asn
Ile Lys Thr Glu Glu Ile Ser Glu Val Lys Met Asp
Ala Glu Phe Arg His Asp Ser Gly Tyr Glu Val His
His Gln Lys Leu Val Phe Phe Ala Glu Asp Val Gly
Ser Asn Lys Gly Ala Ile Ile Gly Leu Met Val Gly
Gly Val Val Ile Ala Thr Val Ile Val Ile Thr Leu
Val Met Leu Lys Lys Lys Gln Tyr Thr Ser Ile 645
650 655 His His Gly Val Val Glu Val Asp Ala Ala
Val Thr Pro Glu Glu Arg His Leu Ser Lys Met Gln
Gln Asn Gly Tyr Glu Asn Pro Thr Tyr Lys Phe Phe
Glu Gln Met Gln Asn
```

The above examples are illustrative only and do not define the invention; other variants will be readily apparent to those of ordinary skill in the art. The scope of the invention is encompassed by the claims of any patent(s) issuing herefrom. The scope of the invention should, therefore, be determined not with reference to the above description, but instead should be determined with reference to the issued claims along with their full scope of equivalents. All publications, references, and patent documents cited in this application are incorporated by reference in their entirety for all purposes to the same extent as if each individual publication or patent document were so individually denoted.

What is claimed is:

1. An isolated human, humanized, or chiineric antibody that specifically binds to an epitope within
   residues 551-570 of human amyloid precursor protein (APP695 numbering);
   residues 530-580 of human amyloid precursor protein (APP695 numbering); or
   residues 545-555 of human amyloid precursor protein (APP695 numbering).

2. The antibody of claim 1 that is a monoclonal antibody.

* * * * *

SEQUENCE LISTING

<160> NUMBER OF SEQ ID NOS: 11

<210> SEQ ID NO 1
<211> LENGTH: 42
<212> TYPE: PRT
<213> ORGANISM: Homo sapiens

<400> SEQUENCE: 1

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 2
<211> LENGTH: 695
<212> TYPE: PRT
<213> ORGANISM: Homo sapiens

<400> SEQUENCE: 2

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
        100                 105                 110

Ile Pro Tyr Arg Cys Leu Val Gly Glu Phe Val Ser Asp Ala Leu Leu
    115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335
```

```
Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
        370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro Arg His Val Phe
                    405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
        450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                    485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                    565                 570                 575

Thr Arg Pro Gly Ser Gly Leu Thr Asn Ile Lys Thr Glu Glu Ile Ser
                580                 585                 590

Glu Val Lys Met Asp Ala Glu Phe Arg His Asp Ser Gly Tyr Glu Val
            595                 600                 605

His His Gln Lys Leu Val Phe Phe Ala Glu Asp Val Gly Ser Asn Lys
        610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                    645                 650                 655

His His Gly Val Val Glu Val Asp Ala Ala Val Thr Pro Glu Glu Arg
                660                 665                 670

His Leu Ser Lys Met Gln Gln Asn Gly Tyr Glu Asn Pro Thr Tyr Lys
            675                 680                 685

Phe Phe Glu Gln Met Gln Asn
        690                 695

<210> SEQ ID NO 3
<211> LENGTH: 16
<212> TYPE: PRT
<213> ORGANISM: Plasmodium sp.

<400> SEQUENCE: 3

Glu Lys Lys Ile Ala Lys Met Glu Lys Ala Ser Ser Val Phe Asn Val
1               5                   10                  15
```

```
<210> SEQ ID NO 4
<211> LENGTH: 10
<212> TYPE: PRT
<213> ORGANISM: Hepatitis B virus

<400> SEQUENCE: 4

Phe Phe Leu Leu Thr Arg Ile Leu Thr Ile
1               5                   10

<210> SEQ ID NO 5
<211> LENGTH: 19
<212> TYPE: PRT
<213> ORGANISM: Mycobacterium sp.

<400> SEQUENCE: 5

Asp Gln Ser Ile Gly Asp Leu Ile Ala Glu Ala Met Asp Lys Val Gly
1               5                   10                  15

Asn Glu Gly

<210> SEQ ID NO 6
<211> LENGTH: 14
<212> TYPE: PRT
<213> ORGANISM: Bacillus sp.

<400> SEQUENCE: 6

Gln Val His Phe Gln Pro Leu Pro Pro Ala Val Val Lys Leu
1               5                   10

<210> SEQ ID NO 7
<211> LENGTH: 15
<212> TYPE: PRT
<213> ORGANISM: Clostridium tetani

<400> SEQUENCE: 7

Gln Tyr Ile Lys Ala Asn Ser Lys Phe Ile Gly Ile Thr Glu Leu
1               5                   10                  15

<210> SEQ ID NO 8
<211> LENGTH: 21
<212> TYPE: PRT
<213> ORGANISM: Clostridium tetani

<400> SEQUENCE: 8

Phe Asn Asn Phe Thr Val Ser Phe Trp Leu Arg Val Pro Lys Val Ser
1               5                   10                  15

Ala Ser His Leu Glu
            20

<210> SEQ ID NO 9
<211> LENGTH: 16
<212> TYPE: PRT
<213> ORGANISM: Human immunodeficiency virus

<400> SEQUENCE: 9

Lys Gln Ile Ile Asn Met Trp Gln Glu Val Gly Lys Ala Met Tyr Ala
1               5                   10                  15

<210> SEQ ID NO 10
<211> LENGTH: 153
<212> TYPE: PRT
<213> ORGANISM: Homo sapiens

<400> SEQUENCE: 10
```

```
Asp Pro Lys Lys Ala Ala Gln Ile Arg Ser Gln Val Met Thr His Leu
1               5                   10                  15

Arg Val Ile Tyr Glu Arg Met Asn Gln Ser Leu Ser Leu Leu Tyr Asn
            20                  25                  30

Val Pro Ala Val Ala Glu Glu Ile Gln Asp Glu Val Asp Glu Leu Leu
            35                  40                  45

Gln Lys Glu Gln Asn Tyr Ser Asp Asp Val Leu Ala Asn Met Ile Ser
    50                  55                  60

Glu Pro Arg Ile Ser Tyr Gly Asn Asp Ala Leu Met Pro Ser Leu Thr
65                  70                  75                  80

Glu Thr Lys Thr Thr Val Glu Leu Leu Pro Val Asn Gly Glu Phe Ser
            85                  90                  95

Leu Asp Asp Leu Gln Pro Trp His Ser Phe Gly Ala Asp Ser Val Pro
            100                 105                 110

Ala Asn Thr Glu Asn Glu Val Glu Pro Val Asp Ala Arg Pro Ala Ala
            115                 120                 125

Asp Arg Gly Leu Thr Thr Arg Pro Gly Ser Gly Leu Thr Asn Ile Lys
            130                 135                 140

Thr Glu Glu Ile Ser Glu Val Lys Met
145                 150

<210> SEQ ID NO 11
<211> LENGTH: 13
<212> TYPE: PRT
<213> ORGANISM: Artificial
<220> FEATURE:
<223> OTHER INFORMATION: PADRE T-cell epitope
<220> FEATURE:
<221> NAME/KEY: misc_feature
<222> LOCATION: (3)..(3)
<223> OTHER INFORMATION: Xaa can be any naturally occurring amino acid

<400> SEQUENCE: 11

Ala Lys Xaa Val Ala Ala Trp Thr Leu Lys Ala Ala Ala
1               5                   10
```